(12) United States Patent
Sakaguchi et al.

(10) Patent No.: US 10,779,786 B2
(45) Date of Patent: Sep. 22, 2020

(54) MEDICAL INFORMATION PROCESSING APPARATUS, X-RAY CT APPARATUS, AND MEDICAL INFORMATION PROCESSING METHOD

(71) Applicant: CANON MEDICAL SYSTEMS CORPORATION, Otawara-shi (JP)

(72) Inventors: Takuya Sakaguchi, Utsunomiya (JP); Takahiko Nishioka, Otawara (JP); Kazumasa Arakita, Utsunomiya (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 61 days.

(21) Appl. No.: 15/724,455

(22) Filed: Oct. 4, 2017

(65) Prior Publication Data
US 2018/0092615 A1    Apr. 5, 2018

(30) Foreign Application Priority Data

Oct. 4, 2016 (JP) .................................. 2016-196804
Aug. 10, 2017 (JP) .................................. 2017-155989

(51) Int. Cl.
*A61B 6/00* (2006.01)
*A61B 5/02* (2006.01)
(Continued)

(52) U.S. Cl.
CPC ............ *A61B 6/5217* (2013.01); *A61B 5/004* (2013.01); *A61B 5/026* (2013.01);
(Continued)

(58) Field of Classification Search
CPC ..... A61B 6/504; A61B 5/02007; A61B 5/026; A61B 8/06; A61B 8/0891;
(Continued)

(56) References Cited

U.S. PATENT DOCUMENTS 9,314,584 B1* 4/2016 Riley .................... A61M 25/00
2012/0041739 A1  2/2012 Taylor
(Continued)

FOREIGN PATENT DOCUMENTS

JP        2013-534154          9/2013
WO   WO 2013/031741 A1    3/2013

*Primary Examiner* — Kenny A Cese
(74) *Attorney, Agent, or Firm* — Oblon, McClelland, Maier & Neustadt, L.L.P.

(57) ABSTRACT

A medical information processing apparatus according to an embodiment includes processing circuitry. The processing circuitry obtains image data rendering a blood vessel of patient. The processing circuitry performs a fluid analysis on the obtained image data and calculates an index value related to a blood flow in the blood vessel with respect to each of a plurality of positions in the blood vessel. With respect to the index values to be calculated, the processing circuitry selects a position in which a first value is to be obtained from among the plurality of positions or selects a value serving as the first value from among the index values exhibited in positions. The processing circuitry causes a display to display the first value in a predetermined display region thereof used for displaying the first value.

31 Claims, 23 Drawing Sheets

(51) Int. Cl.
| | |
|---|---|
| *A61B 8/06* | (2006.01) |
| *A61B 8/08* | (2006.01) |
| *G06T 7/00* | (2017.01) |
| *G16B 5/00* | (2019.01) |
| *A61B 6/03* | (2006.01) |
| *A61B 34/10* | (2016.01) |
| *G06T 11/00* | (2006.01) |
| *A61B 5/00* | (2006.01) |
| *A61B 5/026* | (2006.01) |
| *G16H 50/50* | (2018.01) |
| *A61B 5/029* | (2006.01) |
| *A61B 5/107* | (2006.01) |
| *G06F 19/00* | (2018.01) |
| *A61B 6/12* | (2006.01) |
| *A61B 8/00* | (2006.01) |

(52) U.S. Cl.
CPC .......... *A61B 5/02007* (2013.01); *A61B 5/029* (2013.01); *A61B 5/1079* (2013.01); *A61B 5/7275* (2013.01); *A61B 6/032* (2013.01); *A61B 6/504* (2013.01); *A61B 6/5229* (2013.01); *A61B 8/06* (2013.01); *A61B 34/10* (2016.02); *G06F 19/321* (2013.01); *G06T 7/0012* (2013.01); *G06T 11/008* (2013.01); *G16B 5/00* (2019.02); *G16H 50/50* (2018.01); *A61B 6/037* (2013.01); *A61B 6/12* (2013.01); *A61B 6/463* (2013.01); *A61B 6/563* (2013.01); *A61B 8/085* (2013.01); *A61B 8/0891* (2013.01); *A61B 8/463* (2013.01); *A61B 8/5223* (2013.01); *A61B 2034/101* (2016.02); *G06T 2207/10081* (2013.01); *G06T 2207/20036* (2013.01); *G06T 2207/30048* (2013.01); *G06T 2211/404* (2013.01); *Y02A 90/26* (2018.01)

(58) Field of Classification Search
CPC ......... G06T 2207/30104; G06T 7/0012; G06T 2207/30101; G06T 2207/10081; G06T 2207/10116
See application file for complete search history.

(56) References Cited

U.S. PATENT DOCUMENTS

| | | | |
|---|---|---|---|
| 2014/0276036 A1* | 9/2014 | Collins | A61B 5/02007 600/431 |
| 2014/0316758 A1 | 10/2014 | Yagi et al. | |
| 2014/0350350 A1* | 11/2014 | Imagawa | A61B 6/12 600/300 |
| 2014/0350393 A1* | 11/2014 | Ichihara | A61B 5/029 600/425 |
| 2015/0038860 A1* | 2/2015 | Fonte | A61B 5/026 600/505 |
| 2015/0161790 A1* | 6/2015 | Takahashi | A61B 6/507 600/424 |
| 2015/0245776 A1* | 9/2015 | Hirohata | A61B 6/032 600/504 |
| 2016/0196666 A1* | 7/2016 | Venkatraghavan | G06T 7/254 382/130 |

\* cited by examiner

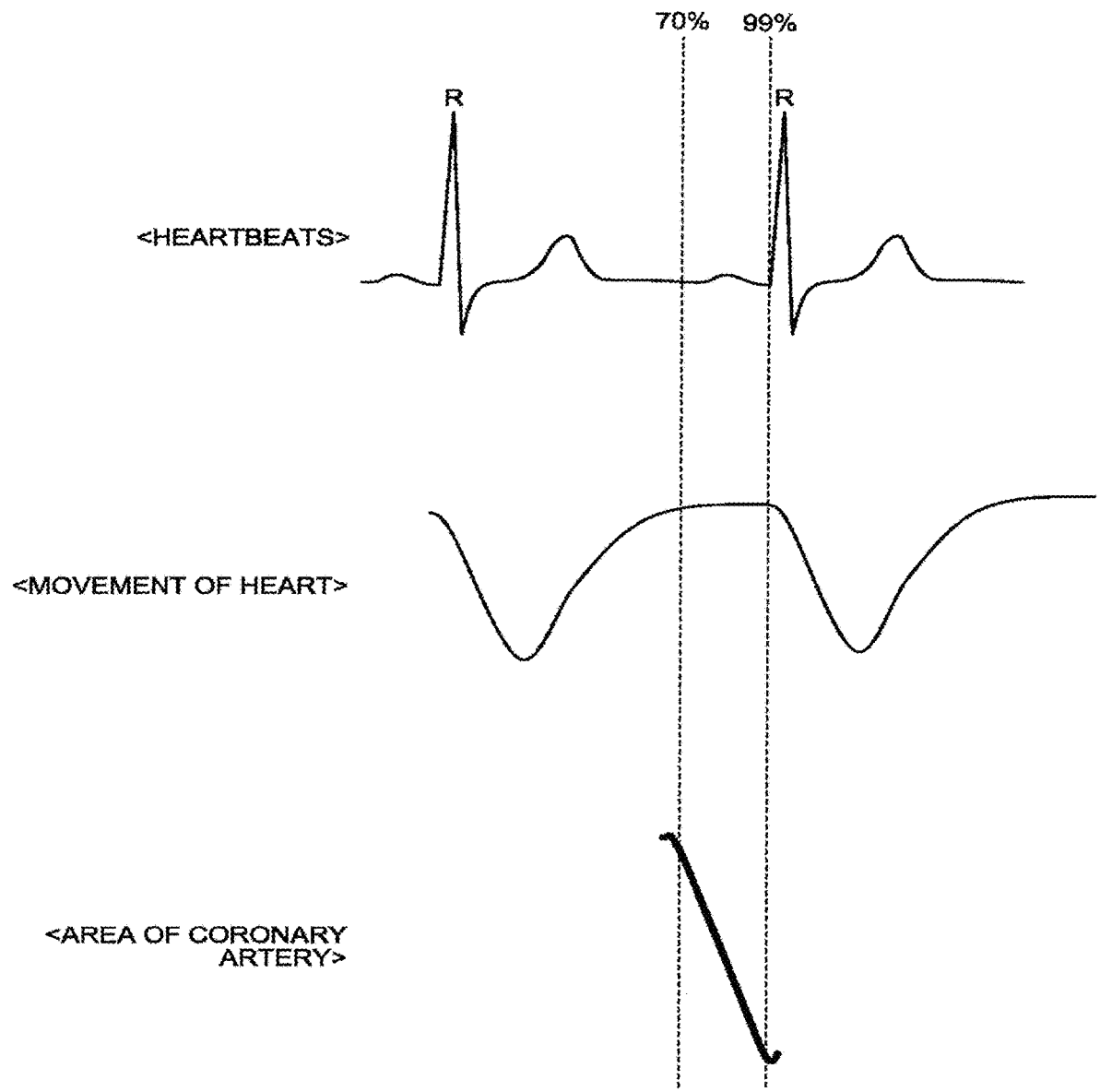

FIG.5A

```
LAD: 0.26
LCX: 0.97
RCA: 0.70
```
(340)

FIG.8A
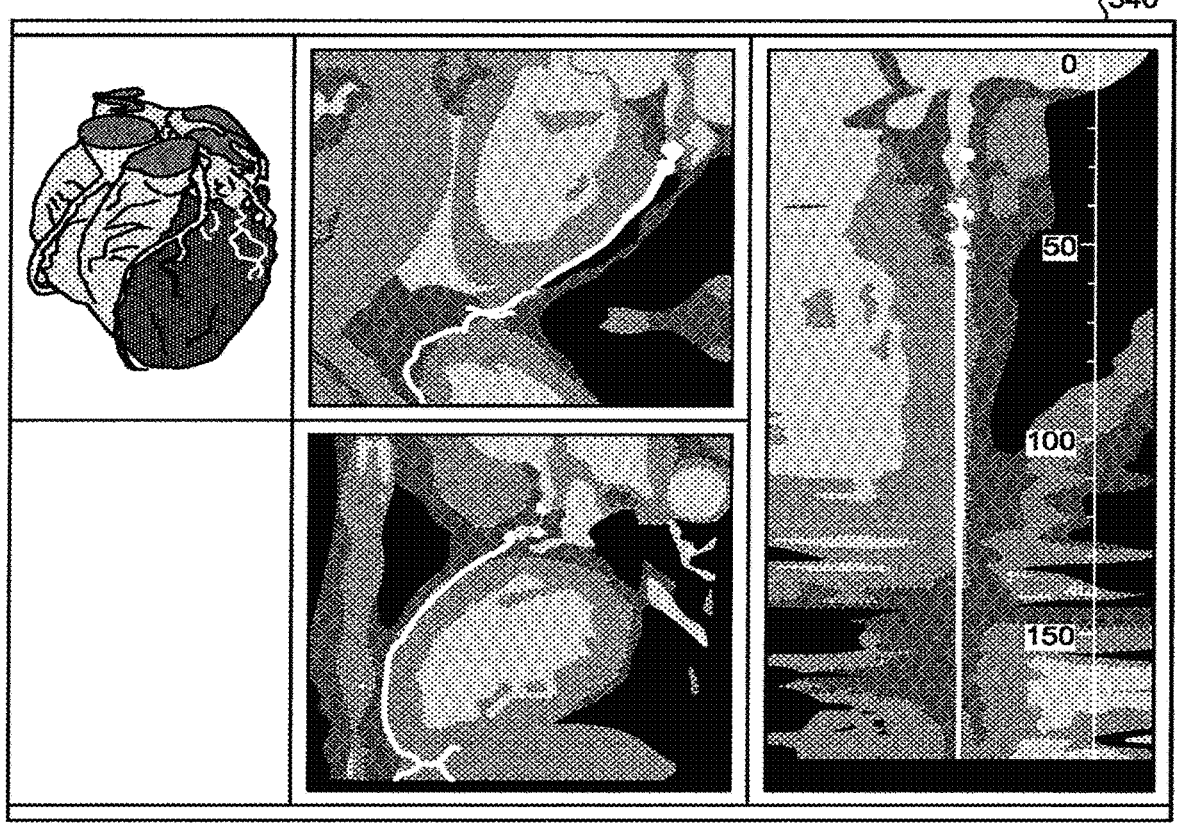
FFR: 0.73

FIG.8B
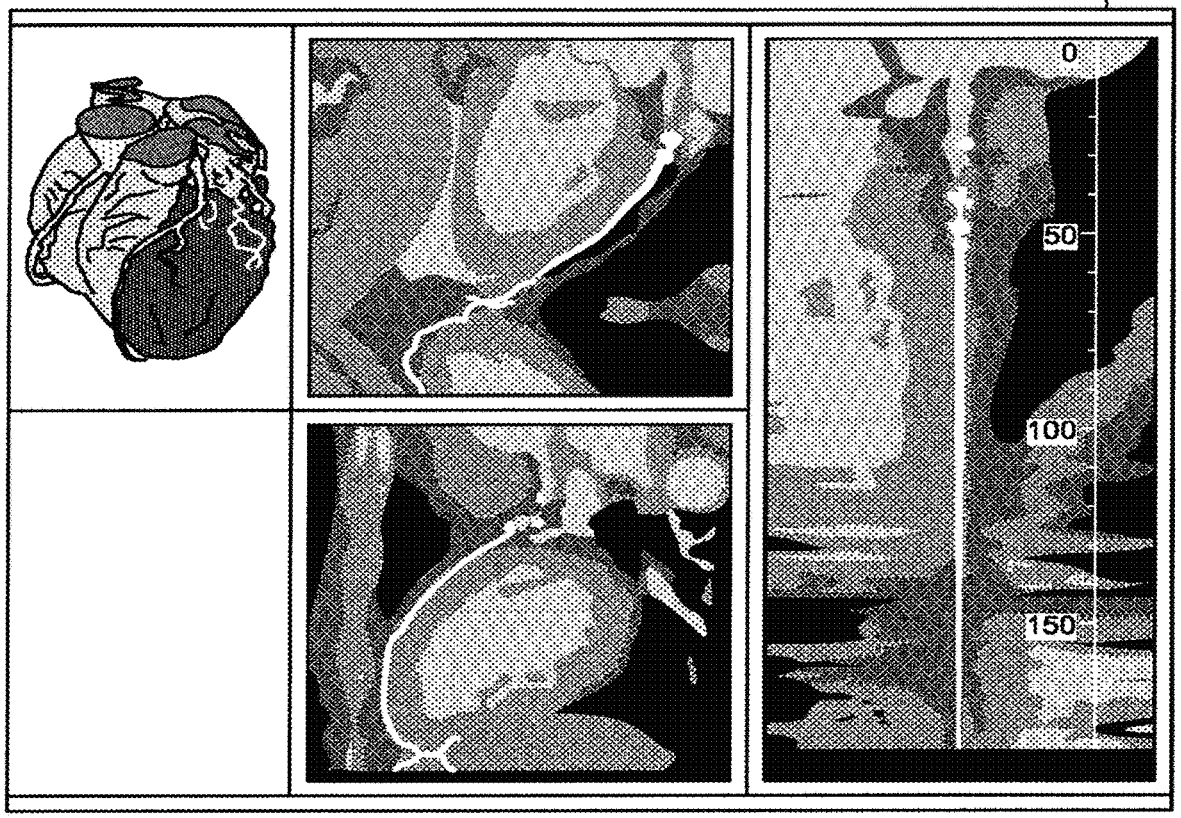
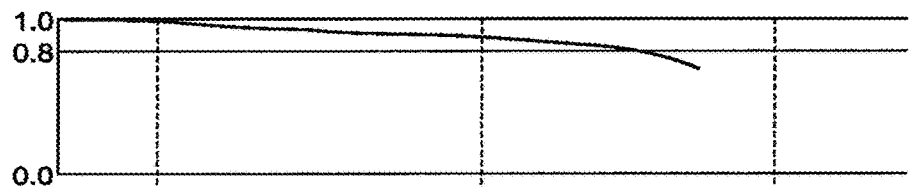

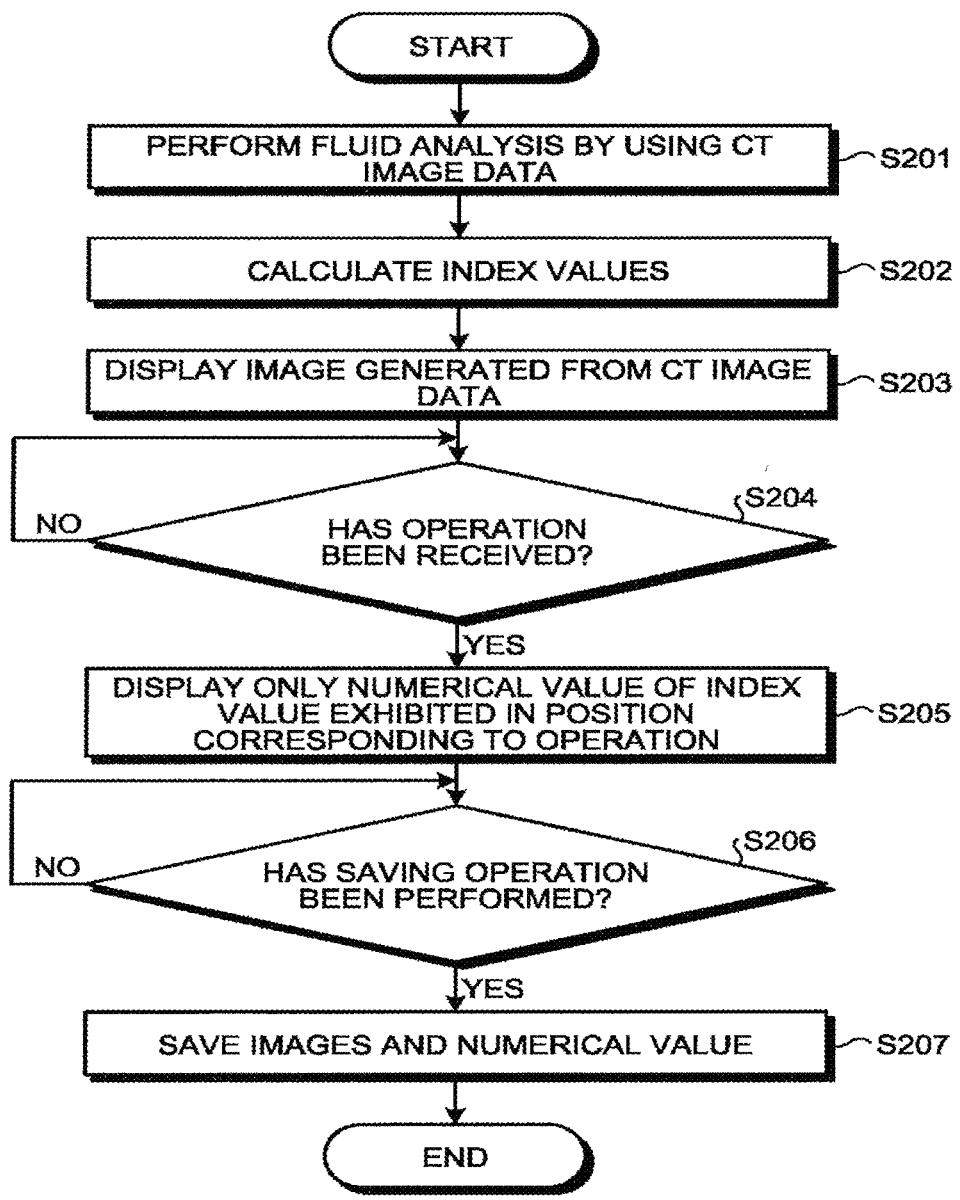

FIG.11A

LAD
FFR: 0.26  △FFR: 0.3
LCX
FFR: 0.97  △FFR: 0.1
RCA
FFR: 0.70  △FFR: 0.11

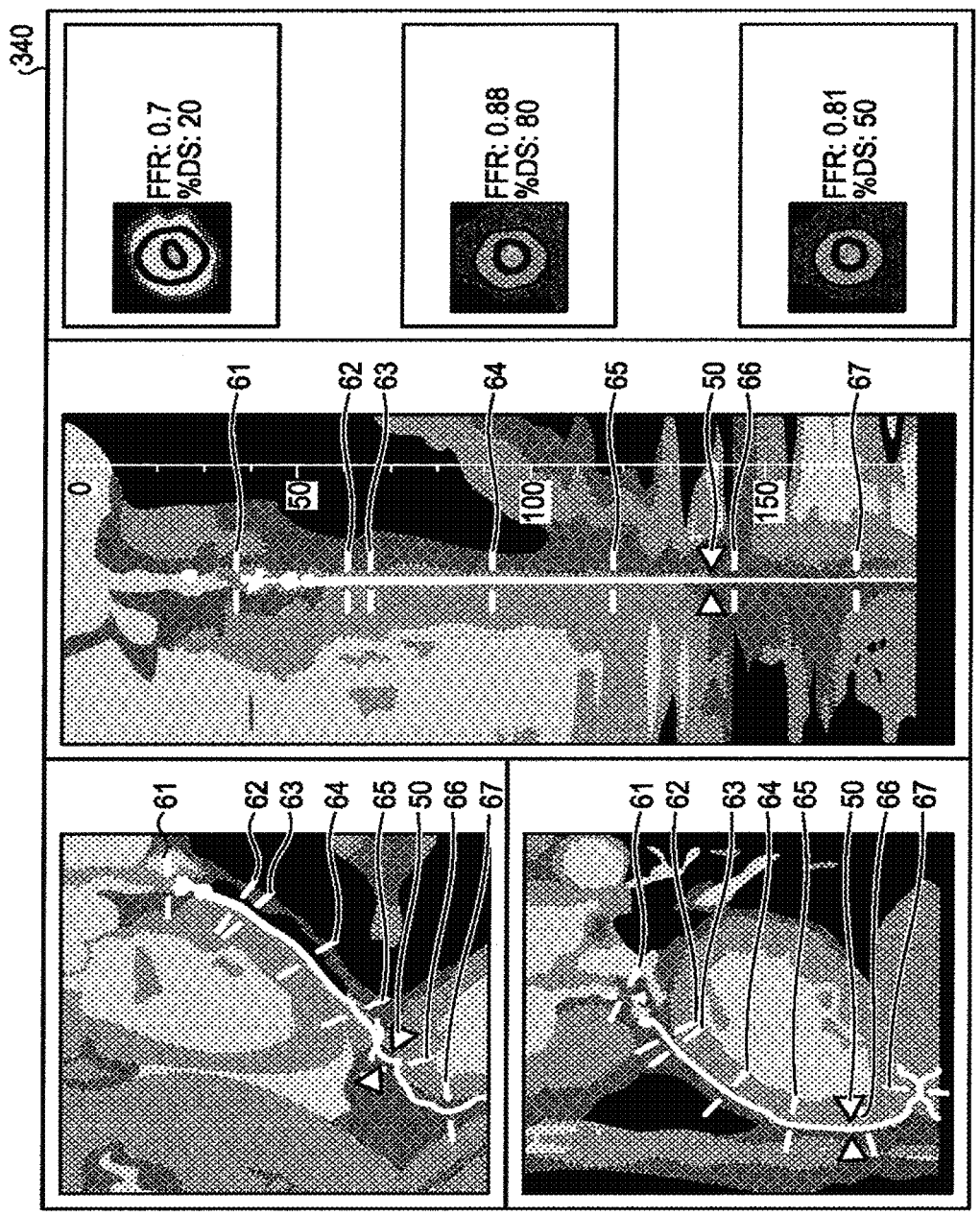

FIG.15A
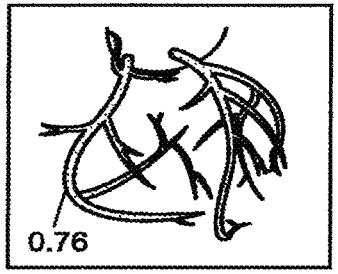
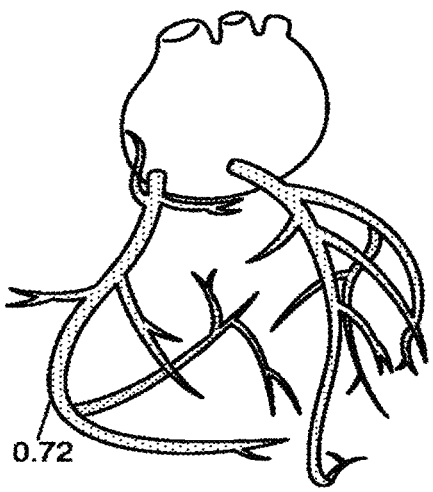

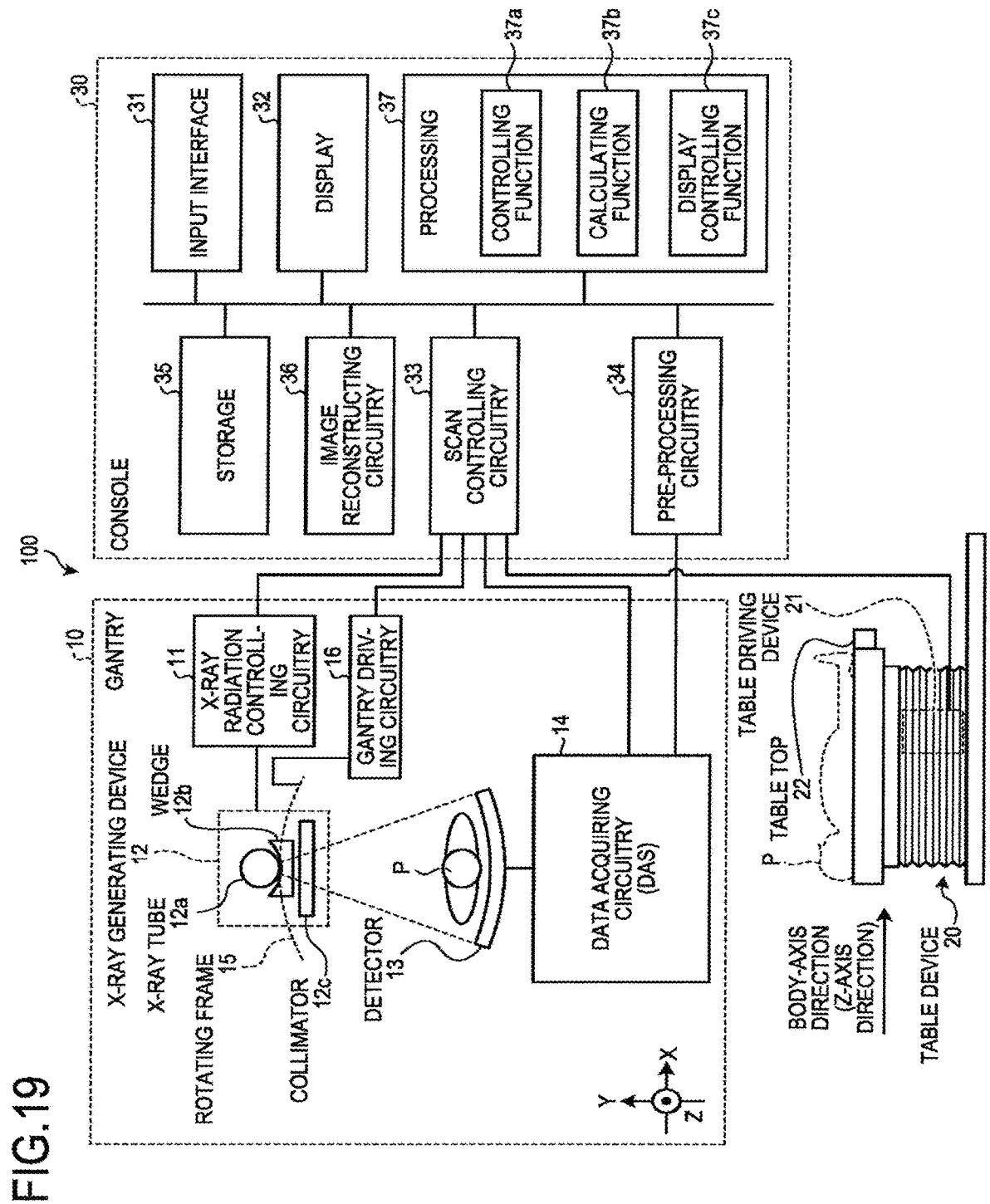

MEDICAL INFORMATION PROCESSING APPARATUS, X-RAY CT APPARATUS, AND MEDICAL INFORMATION PROCESSING METHOD

CROSS-REFERENCE TO RELATED APPLICATIONS

This application is based upon and claims the benefit of priority from Japanese Patent Application No. 2016-196804, filed on Oct. 4, 2016 and Japanese Patent Application No. 2017-155989, Filed on Aug. 10, 2017; the entire contents of which are incorporated herein by reference.

FIELD

Embodiments described herein relate generally to a medical information processing apparatus, an X-ray CT apparatus, and a medical information processing method.

BACKGROUND

It has conventionally been known that causes of ischemic diseases of organs include, in a rough classification, blood circulation disorders and functional disorders of the organs themselves. For example, a stenosis, which is an example of a blood circulation disorder in a coronary artery, is a serious lesion that may lead to an ischemic heart disease. For such an ischemic heart disease, it is necessary to judge whether a treatment should be performed with drugs, with a stent, or the like. In recent years, as a diagnosing process to evaluate ischemia related to blood circulation in coronary arteries, there is a trend that a recommended method is to measure a Fractional Flow Reserve (FFR) value by using a pressure wire during a Coronary Angiography (CAG) examination that uses a catheter.

In contrast, for example, other methods are also known by which ischemia related to blood circulation in coronary arteries is evaluated in a non-invasive manner by using a medical image of the heart acquired by using a medical image diagnosis apparatus such as an X-ray Computed Tomography (CT) apparatus, a Magnetic Resonance Imaging (MRI) apparatus, an ultrasound diagnosis apparatus, or the like. As explained herein, ischemic related to blood circulation is evaluated by using various methods, and treatments are each performed in accordance with the evaluation. In recent years, there is a demand that the actual effects of treatments be assessed prior to the application of each treatment.

BRIEF DESCRIPTION OF THE DRAWINGS

FIG. 4 is a drawing for explaining a temporal phase used in a fluid analysis according to the first embodiment;

FIG. 5A is a drawing illustrating an example of a display of FFR values realized by a display controlling function according to the first embodiment;

FIG. 5B is a drawing illustrating another example of the display of FFR values realized by the display controlling function according to the first embodiment;

FIG. 8A is a drawing illustrating an example of a display switching process performed by a display controlling function according to a second embodiment;

FIG. 8B is a drawing illustrating another example of the display switching process performed by the display controlling function according to the second embodiment;

FIG. 9 is a flowchart illustrating a processing procedure performed by a medical information processing apparatus according to the second embodiment;

FIG. 11A is a drawing illustrating an example of a display of supplementary information realized by a display controlling function according to the third embodiment;

FIG. 11C is a drawing illustrating yet another example of the display of supplementary information realized by the display controlling function according to the third embodiment;

FIG. 15A is a drawing for explaining an example of a representative value according to a fifth embodiment;

FIG. 19 is a diagram illustrating an exemplary configuration of an X-ray CT apparatus according to the fifth embodiment.

DETAILED DESCRIPTION

Exemplary embodiments of a medical information processing apparatus, an X-ray CT apparatus, and a medical information processing method of the present disclosure will be explained in detail below, with reference to the accompanying drawings. Possible embodiments of the medical information processing apparatus, the X-ray CT apparatus, and the medical information processing method of the present disclosure are not limited to the embodiments described below.

First Embodiment

To begin with, a first embodiment will be explained. In the first embodiment, an example will be explained in which technical features of the present disclosure are applied to a medical information processing apparatus. In the following sections, a medical information processing system including the medical information processing apparatus will be explained as an example. Further, in the following sections, as an example, a situation will be explained in which a blood vessel of the heart serves as a target of an analysis.

Figure 1:
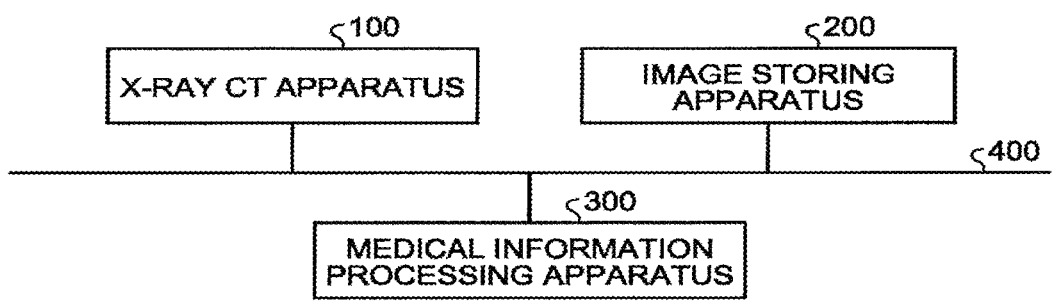
FIG. 1 is a diagram illustrating an exemplary configuration of a medical information processing system according to a first embodiment.

FIG. 1 is a diagram illustrating an exemplary configuration of a medical information processing system according to the first embodiment. As illustrated in FIG. 1, the medical information processing system according to the first embodiment includes an X-ray Computed Tomography (CT) apparatus 100, an image storing apparatus 200, and a medical information processing apparatus 300.

For example, as illustrated in FIG. 1, the medical information processing apparatus 300 according to the first embodiment is connected to the X-ray CT apparatus 100 and to the image storing apparatus 200, via a network 400. Via the network 400, the medical information processing system may further be connected to another medical image diagnosis apparatus such as a Magnetic Resonance Imaging (MRI) apparatus, an ultrasound diagnosis apparatus, a Positron Emission Tomography (PET) apparatus, or the like.

The X-ray CT apparatus 100 is configured to acquire CT image data (volume data) of an examined subject (hereinafter, "patient"). More specifically, the X-ray CT apparatus 100 acquires projection data by moving an X-ray tube and an X-ray detector to revolve while the patient is positioned substantially at the center and detecting X-rays that have passed through the patient. Further, the X-ray CT apparatus 100 generates pieces of three-dimensional CT image data in a time series on the basis of the acquired projection data.

The image storing apparatus 200 is configured to store therein image data acquired by various types of medical image diagnosis apparatuses. For example, the image storing apparatus 200 is realized with a computer device such as a server apparatus. In the present embodiment, the image storing apparatus 200 obtains the CT image data (the volume data) from the X-ray CT apparatus 100 via the network 400 and stores the obtained CT image data into a storage provided either inside or outside the apparatus.

Via the network 400, the medical information processing apparatus 300 is configured to obtain image data from various types of medical image diagnosis apparatuses and to process the obtained image data. For example, the medical information processing apparatus 300 is realized with a computer device such as a workstation. In the present embodiment, the medical information processing apparatus 300 obtains the CT image data from either the X-ray CT apparatus 100 or the image storing apparatus 200 via the network 400 and performs any of various types of image processing processes on the obtained CT image data. Further, the medical information processing apparatus 300 causes the CT image data from either before or after the image processing processes to be displayed on a display device or the like.

Figure 2:
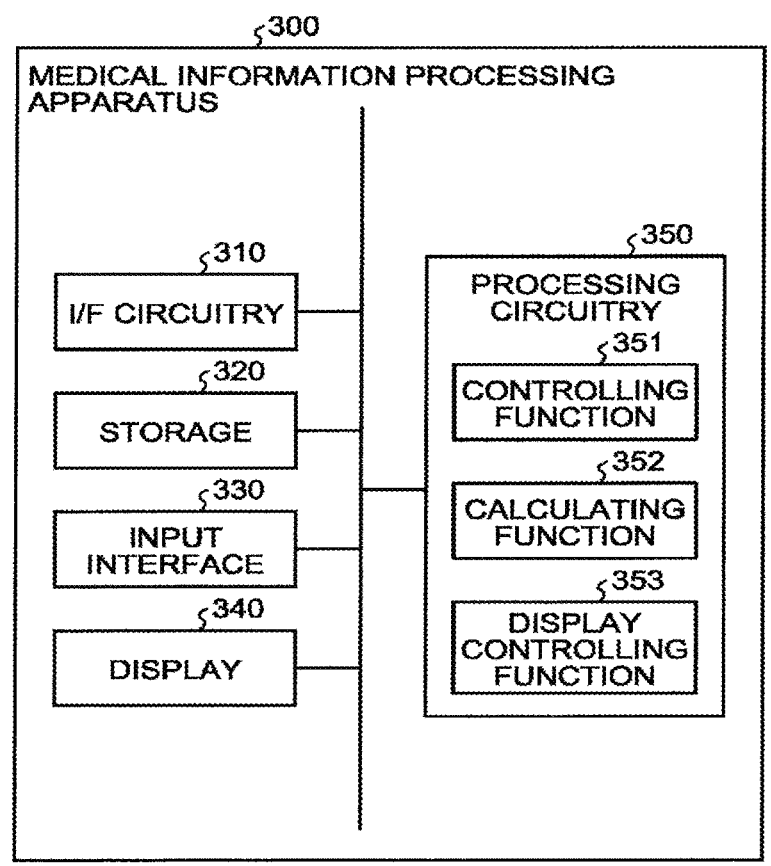
FIG. 2 is a diagram illustrating an exemplary configuration of a medical information processing apparatus according to the first embodiment.

FIG. 2 is a diagram illustrating an exemplary configuration of the medical information processing apparatus 300 according to the first embodiment. For example, as illustrated in FIG. 2, the medical information processing apparatus 300 includes interface (I/F) circuitry 310, a storage 320, an input interface 330, a display 340, and processing circuitry 350.

The I/F circuitry 310 is connected to the processing circuitry 350 and is configured to control transfer and communication of various types of data performed among any of the various types of medical image diagnosis apparatuses and the image storing apparatus 200 that are connected via the network 400. For example, the I/F circuitry 310 is realized with a network card, a network adaptor, a Network Interface Controller (NIC), or the like. In the present embodiment, the I/F circuitry 310 receives the CT image data from either the X-ray CT apparatus 100 or the image storing apparatus 200 and outputs the received CT image data to the processing circuitry 350.

The storage 320 is connected to the processing circuitry 350 and is configured to store therein various types of data. For example, the storage 320 is realized with a semiconductor memory element such as a Random Access Memory (RAM) or a flash memory, a hard disk, an optical disk, or the like. In the present embodiment, the storage 320 stores therein the CT image data received from either the X-ray CT apparatus 100 or the image storing apparatus 200. Further, the storage 320 stores therein processing results obtained by the processing circuitry 350.

The input interface 330 is connected to the processing circuitry 350 and is configured to convert an input operation received from an operator into an electric signal and to output the electric signal to the processing circuitry 350. For example, the input interface 330 is realized with a trackball, a switch button, a mouse, a keyboard, and/or a touch panel.

The display 340 is connected to the processing circuitry 350 and is configured to display various types of information and various types of image data output from the processing circuitry 350. For example, the display 340 is realized with a liquid crystal monitor, a Cathode Ray Tube (CRT) monitor, a touch panel, or the like.

The processing circuitry 350 is configured to control constituent elements of the medical information processing apparatus 300 in response to the input operation received from the operator via the input interface 330. For example, the processing circuitry 350 is realized with a processor. In the present embodiment, the processing circuitry 350 stores the CT image data output from the I/F circuitry 310 into the storage 320. Further, the processing circuitry 350 reads the CT image data from the storage 320 and causes the display 340 to display the read CT image data.

The medical information processing apparatus 300 according to the present embodiment configured as described above makes it possible to improve efficiency of diagnosing processes related to a blood flow. More specifically, the medical information processing apparatus 300 improves the efficiency of the diagnosing processes by displaying a representative value of an index related to the blood flow and making it possible to promptly perform appropriate diagnosing processes.

To perform the process described above, the processing circuitry 350 included in the medical information processing apparatus 300 according to the first embodiment implements a controlling function 351, a calculating function 352, and a display controlling function 353, as illustrated in FIG. 2. In this situation, the processing circuitry 350 is an example of the processing circuitry set forth in the claims.

The controlling function 351 is configured to exercise overall control of the medical information processing apparatus 300. For example, the controlling function 351 controls various types of processes performed in response to electric signals received from the input interface 330. In one example, the controlling function 351 controls the obtainment of the CT image data via the I/F circuitry 310 and the storing of the obtained CT image data into the storage 320. For example, the controlling function 351 obtains CT image data rendering blood a vessel of the patient and stores the obtained CT image data into the storage 320. Further, for example, the controlling function 351 reads the CT image data stored by the storage 320 and controls generation of a display image from the read CT image data. In an example, by performing various types of image processing processes on the CT image data, the controlling function 351 generates an image of a blood vessel. For example, the controlling function 351 generates a volume rendering image, a Curved Multi Planar Reconstruction (CPR) image, a Multi Planar Reconstruction (MPR) image, a Stretched Multi Planar Reconstruction (SPR) image, and the like by performing image processing processes on the CT image data.

The calculating function 352 is configured to perform a fluid analysis on the basis of the CT image data. More specifically, the calculating function 352 performs a fluid analysis on the CT image data obtained by the controlling function 351 and obtains an index value related to a blood flow in the blood vessel. In this situation, the calculating function 352 has a representative value extracting function configured to extract a representative value (a first value) of various types from the calculated index value. More specifically, with respect to the calculated index value, the calculating function 352 either selects a position in the blood vessel in which the representative value is to be obtained from among a plurality of positions or selects a value serving as the representative value from among index values exhibited in different positions. For example, the calculating function 352 analyzes the shape of the blood vessel of the patient and sets the position in the blood vessel from which the representative value is to be obtained on the basis of the shape of the blood vessel. Further, the calculating function 352 analyzes the shape of the blood vessel of the patient and sets a position away from a distal position of the blood vessel by a predetermined distance, as the position in the blood vessel from which the representative value is to be obtained. Further, the calculating function 352 analyzes the shape of the blood vessel of the patient and sets such a position that has a blood vessel diameter equal to a predetermined value and is closest to the distal end, as the position in the blood vessel from which the representative value is to be obtained. In the embodiments described below, an example will be explained in which the calculating function 352 includes the representative value extracting function and is configured to extract the representative value; however, possible embodiments are not limited to this example. Alternatively, the processing circuitry 350 may implement the representative value extracting function separately from the calculating function 352. Next, details of the calculating function will be explained. For example, the calculating function 352 extracts pieces of blood vessel shape data in a time series indicating the shape of the blood vessel, from three-dimensional CT image data. For example, the calculating function 352 extracts the pieces of blood vessel shape data in the time series by reading, from the storage 320, pieces of CT image data that correspond to a plurality of temporal phases and were acquired chronologically and further performing an image processing process on the read pieces of CT image data corresponding to the plurality of temporal phases.

In this situation, the calculating function 352 sets a target region from which the index related to the blood flow is to be calculated, in a blood vessel region included in the CT image data. More specifically, by following an instruction from the operator received via the input interface 330 or by performing an image processing process, the calculating function 352 sets the target region in the blood vessel region. After that, as blood vessel shape data of the set target region, for example, the calculating function 352 extracts, from the CT image data, a central line (coordinate information of the central line) of the blood vessel, a cross-sectional area of the blood vessel and a lumen on a cross-sectional plane perpendicular to the central line, and the distance from the central line to the internal wall and the distance from the central line to the external wall in the columnar direction on a cross-sectional plane perpendicular to the central line, for example. The calculating function 352 is also capable of extracting various types of other blood vessel shape data by using various analyzing methods.

Further, the calculating function 352 sets analyzing conditions of the fluid analysis. More specifically, as the analyzing conditions, the calculating function 352 sets physical property values of the blood, conditions of a repetitive calculation, and initial values of the analysis. For example, as the physical property values of the blood, the calculating function 352 sets a viscosity value and a density value of the blood. Further, as the conditions of the repetitive calculation, the calculating function 352 sets a maximum number of times of repetition, a relaxation coefficient, and a residual tolerance value, and the like used for the repetitive calculation. Further, as the initial values of the analysis, the calculating function 352 sets initial values for flow rate values, pressure values, fluid resistance values, pressure boundary values, and the like. Various types of values used by the calculating function 352 may be incorporated in the system in advance or may be defined by the operator in an interactive manner.

After that, the calculating function 352 calculates indices related to the blood flow of the blood vessel, by performing the fluid analysis while using the image data rendering a blood vessel (e.g., a coronary artery). More specifically, the calculating function 352 calculates the indices related to the blood flow with respect to the target region of the blood vessel by performing the fluid analysis while using the blood vessel shape data and the analyzing conditions. For example, the calculating function 352 calculates, with respect to each of predetermined positions in the blood vessel, indices indicating pressure, a blood flow rate, a blood flow speed, a vector, a shearing stress, and the like, on the basis of the blood vessel shape data indicating the contours of the lumen and the external wall of the blood vessel as well as the cross-sectional area and the central line of the blood vessel, together with setting conditions such as the physical property values of the blood vessel, the conditions of the repetitive calculation, and the initial values of the analysis. Further, the calculating function 352 calculates temporal fluctuations of the indices indicating the pressure, the blood flow rate, the blood flow speed, the vector, the shearing stress, and the like, by using temporal fluctuations of the blood vessel shape data indicating the contours of the lumen and the external wall of the blood vessel and the cross-sectional area and the central line of the blood vessel.

Figure 3:
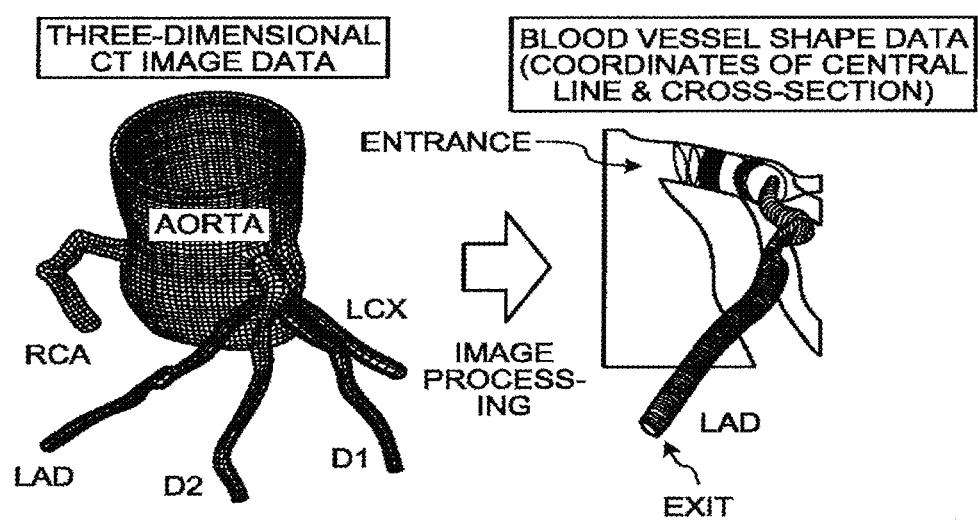
FIG. 3 is a drawing for explaining an example of a process performed by a calculating function according to the first embodiment.

FIG. 3 is a drawing for explaining an example of a process performed by the calculating function 352 according to the first embodiment. As illustrated in FIG. 3, for example, the calculating function 352 extracts blood vessel shape data including the coordinates of the central line and cross-section information with respect to a target region LAD, from three-dimensional CT image data rendering an aorta and coronary arteries. Further, the calculating function 352 sets analyzing conditions of an analysis to be performed on the extracted LAD. Further, by performing a fluid analysis while using the extracted blood vessel shape data of the LAD and the set conditions, the calculating function 352 calculates, for example, the indices indicating the pressure, the blood flow rate, the blood flow speed, the vector, the shearing stress, and the like, for each of the predetermined positions along the central line from the boundary at the entrance to the boundary at the exit of the target region LAD. In other words, with respect to the target region, the calculating function 352 calculates distributions of pressure values, blood flow rate values, blood flow speed values, vectors, shearing stress values, and the like.

As explained above, the calculating function 352 calculates the indices related to the blood flow by extracting the blood vessel shape data from each of the pieces of CT image data that correspond to the plurality of temporal phases and were acquired chronologically and further performing the fluid analysis while using the extracted blood vessel shape data corresponding to the plurality of temporal phases and the analyzing conditions. In this situation, by using pieces of CT image data which correspond to a plurality of temporal phases and of which the cardiac phases are within a predetermined range, the calculating function 352 is able to calculate analysis results with a higher level of precision.

FIG. 4 is a drawing for explaining a temporal phase used in the fluid analysis according to the first embodiment. In FIG. 4, the top section illustrates heartbeats, while the middle section illustrates movement of the heart, and the bottom section illustrates the area of a coronary artery. Further, in FIG. 4, the horizontal direction expresses time, while temporal fluctuations of the heartbeats, the movement of the heart, and the area of the coronary artery are illustrated in correspondence with the time. For example, the calculating function 352 performs the fluid analysis by using CT image data of which the cardiac phase is included in the range of cardiac phase 70% to 99%. In this situation, the cardiac phase 70% to 99% is a temporal phase in which, as illustrated in FIG. 4, the heart makes little movement while the area of the coronary artery changes significantly. Because the heart moves by expansion and contraction, the movement becomes stable in the latter half of diastole periods (corresponding to the cardiac phase 70% to 99%) as illustrated in the middle section of FIG. 4. In other words, by using the CT image data of which the cardiac phase is included the cardiac phase 70% to 99% where the movement is stable, the calculating function 352 is able to use the CT image data in which movement caused by the heartbeats is small.

Further, as illustrated in the bottom section of FIG. 4, the area of the coronary artery is at a maximum near the cardiac phase 70% and is at a minimum near the cardiac phase 99%. The reason is that blood starts flowing into the coronary artery near the cardiac phase 70% and subsequently blood keeps flowing out as the cardiac phase progresses toward 99%. The calculating function 352 calculates an analysis result with a higher level of precision by using the CT image data corresponding to the plurality of temporal phases in range of cardiac phase 70% to 99% so as to include as muuch change in the area of the coronary artery as possible.

Further, on the basis of the distribution of the pressure values in the target region, the calculating function 352 calculates a Fractional Flow Reserve (FFR) value. In other words, the calculating function 352 calculates the FFR value that is an index used for estimating how much the blood flow is obstructed by a lesion, on the basis of the pressure value on the upstream side and the pressure value on the downstream side of a predetermined position (e.g., a lesion site having a stenosis or a plaque) within the blood vessel. In this situation, the calculating function 352 of the present disclosure is capable of calculating any of various types of pressure indices as the FFR value.

Next, a definition of the FFR value will be explained at first. As mentioned above, the FFR value is an index used for estimating how much the blood flow is obstructed by a lesion (e.g., a stenosis or a plaque) and may be defined as a ratio between a flow rate in the absence of the lesion and a flow rate in the presence of the lesion, which can be calculated by using Expression (1) below. In Expression (1), the symbol "Qn" denotes a flow rate in the absence of the lesion, whereas the symbol "Qs" denotes a flow rate in the presence of the lesion.

$$FFR \equiv \frac{Qs}{Qn} \quad (1)$$

For example, the FFR value may be defined by using the expression in which "Qs" is divided by "Qn" as indicated in Expression (1). In this situation, generally speaking, to calculate an FFR value, it is possible to substitute the FFR value with a definition of pressure by administering adenosine to the patient to cause a maximum hyperemia state (a stress state) and arranging the relationship between the flow rate and the pressure within the blood vessel to be a proportional relationship. In other words, by arranging the relationship between the flow rate and the pressure within the blood vessel to be a proportional relationship, it is possible to express Expression (1) with Expression (2) as presented below. In Expression (2), the symbol "Pa" denotes the pressure on the upstream side of the lesion, whereas the symbol "Pd" denotes the pressure on the downstream side of the lesion. Further, the symbol "Pv" denotes pressure in the right atrium into which a flow of venous blood from the entire body enters.

$$FFR \equiv \frac{Qs}{Qn} = \frac{Pd - Pv}{Pa - Pv} \quad (2)$$

For example, by arranging the relationship between the flow rate and the pressure within the blood vessel to be a proportional relationship, it is possible to express "Qs" as "Pd−Pv" and "Qn" as "Pa−Pv", as indicated in Expression (2). In other words, it is possible to express the FFR value as a ratio between a value obtained by subtracting the blood vessel baseline pressure from the pressure on the upstream side of the lesion and a value obtained by subtracting the blood vessel baseline pressure from the pressure on the downstream side of the lesion.

In this situation, in the stress state achieved by administering adenosine to the patient, it is considered that "Pa>>Pv" and "Pd>>Pv" are satisfied. Accordingly, it is possible to regard Expression (2) as indicated in Expression (3).

$$FFR \equiv \frac{Qs}{Qn} = \frac{Pd-Pv}{Pa-Pv} \approx \frac{Pd}{Pa} \quad (3)$$

In other words, as indicated in Expression (3), the FFR value is calculated by using the expression in which "Pd" is divided by "Pa". For example, the calculating function 352 calculates an FFR value in each of different positions in the blood vessel by assigning the calculated pressure on the upstream side of the lesion and the calculated pressure on the downstream side of the lesion to Expression (3) presented above.

In the calculation of the FFR value described above, the example is explained in which the FFR value is substituted with the definition of the pressure, by administering adenosine to the patient to cause the stress state and arranging the relationship between the flow rate and the pressure within the blood vessel to be the proportional relationship. However, to calculate an FFR value, another method is also acceptable by which the FFR value is substituted by a definition of pressure while the patient is in a resting state. In that situation, even while the patient is in a resting state without having adenosine administered, the relationship between the flow rate and the pressure within the blood vessel is a proportional relationship during wave-free periods (when the vascular resistance is small and stable) in the cardiac cycle. Accordingly, an FFR value can be calculated by using the pressure during a wave-free period while the patient is in a resting state. (The FFR value calculated in a wave-free period while the patient is in a resting state may hereinafter be referred to as an "instantaneous FFR value".)

The instantaneous FFR value is an index value attracting attention in recent years, because it is possible to reduce burdens on patients for not having to administer adenosine to the patients, and also, because instantaneous FFR value has some characteristics which an FFR value does not have. (For example, an instantaneous FFR value reflects impacts of myocardium, and it is possible to measure an instantaneous FFR value even when there are two or more stenoses in a single blood vessel.) To calculate an FFR value by using image data, the CT image data corresponding to the cardiac phase 70% to 99% explained above is used as the CT image data in a wave-free period. In other words, the relationship between the flow rate and the pressure within the blood vessel is a proportional relationship in the cardiac phase 70% to 99%. Accordingly, by using the CT image data in this range, it is possible to calculate an FFR value based on the pressure while using Expression (3) above, even when the CT image data is acquired from the patient in the resting state.

Further, by using a zero-flow-rate pressure "P0", which is intravascular pressure corresponding to the time when the flow rate within the blood vessel is equal to "0", as the baseline to be subtracted from the pressure on the upstream side and the pressure on the downstream side of the lesion, the calculating function 352 is able to express the proportional relationship between the flow rate and the pressure more accurately than when using the pressure "Pv" in the right atrium as the baseline. In this situation, by assigning the pressure on the upstream side of the lesion site, the pressure on the downstream side of the lesion site, and the zero-flow-rate pressure to Expression (4) presented below, the calculating function 352 calculates an FFR value in each of different positions in the blood vessel. In Expression (4), the symbol "Pa" denotes the pressure on the upstream side of the lesion (e.g., a stenosis), whereas the symbol "Pd" denotes the pressure on the downstream side of the lesion (e.g., the stenosis). Further, in Expression (4), the symbol "P0" denotes the zero-flow-rate pressure. In this situation, the zero-flow-rate pressure is estimated by searching for a pressure value with which the flow rate and the flow speed become zero, in the fluid analysis performed by the calculating function 352.

$$FFR \equiv \frac{Qs}{Qn} = \frac{Pd-P0}{Pa-P0} \quad (4)$$

In this situation, the value of the zero-flow-rate pressure "P0" is larger than the value of "Pv" both in the stress state and in the resting state, because of a blood vessel resistance. Even when "P0>Pv" is satisfied, blood stops flowing and the flow rate becomes equal to zero. Further, the value of "P0" during a wave-free period in the resting state is larger than the value of "P0" in the stress state, because a difference occurs in the myocardial resistance between the stress state and the resting state. For example, when the blood vessel is expanded in the stress state, the value of "P0" corresponding to zero blood flow is closer to the value of "Pv" in comparison to the value thereof in the resting state, because the resistance is smaller. In contrast, in the resting state, because the resistance is larger than the resistance in the stress state, the value of "P0" corresponding to zero blood flow is larger than the value of "Pv". Accordingly, for example, when CT image data in a wave-free period in the resting state is used, the calculating function 352 calculates an FFR value on the basis of an expression that takes "P0" into consideration, as indicated in Expression (4).

Alternatively, when using the CT image data in a wave-free period in the resting state, the calculating function 352 may calculate an FFR value by using Expression (2) presented above. In that situation, the calculating function 352 calculates an FFR value in each of different positions in the blood vessel by assigning the pressure on the upstream side of the lesion site, the pressure on the downstream side of the lesion site, and "Pv" to Expression (2). In the following sections, the pressure indices mentioned above will collectively be referred to as FFR values.

As explained above, the calculating function 352 calculates the various types of indices related to the blood flow by performing the fluid analysis on the CT image data that correspond to the plurality of temporal phases and were acquired chronologically. In this situation, the calculating function 352 calculates the representative value of the index values related to the blood flow. For example, the calculating function 352 calculates, as the representative value, at least one selected from between: the FFR value obtained at the distal-side end of the target region subject to the fluid analysis within the blood vessel; and the smallest FFR value in the blood vessel. In this situation, for example, the calculating function 352 calculates the representative FFR value for each of the blood vessels rendered in the CT image data. Further, for example, the calculating function 352 calculates a representative FFR value with respect to either each of predetermined regions or each of sections defined by a predetermined distance in the blood vessel.

Returning to FIG. 2, the display controlling function 353 causes the display 340 to display the representative values in a predetermined display region thereof used for displaying the representative values. More specifically, when the calculating function 352 has performed the fluid analysis, the display controlling function 353 causes the display 340 to automatically display the representative FFR values calculated by performing the fluid analysis. Next, examples of the display of the FFR values realized by the display controlling function 353 will be explained, with reference to FIGS. 5A to 5D. FIGS. 5A to 5D are drawings illustrating the examples of the display of the FFR values realized by the display controlling function 353 according to the first embodiment.

For example, when the calculating function 352 has performed the fluid analysis, the display controlling function 353 automatically extracts only representative FFR values (LAD: 0.26; LCX: 0.97; and RCA: 0.70) each corresponding to a different one of the blood vessel branches of the coronary artery and causes the display 340 to display the extracted representative values, as illustrated in FIG. 5A. In this situation, when the calculating function 352 has performed the fluid analysis, the display controlling function 353 automatically causes only the representative FFR values to be displayed, instead of displaying a clinical image of the blood vessel or a three-dimensional model generated from a clinical image. Accordingly, for example, a medical doctor is able to immediately recognize that the Left Anterior Descending (LAD) artery includes a lesion and that the degree of the lesion is severe, by referring to the representative values automatically displayed as illustrated in FIG. 5A. It is therefore possible to save the trouble of designating a position within a three-dimensional model from which the medical doctor wishes to obtain FFR values.

In this situation, the display controlling function 353 is able to display any of the various types of representative values or each of the blood vessel branches. For example, as the representative values, the display controlling function 353 displays an FFR value obtained at the distal-side end (the tip end side) of the target region subject to the fluid analysis with respect to each of the blood vessel branches such as the LAD, the Left Circumflex (LCX) artery, and the Right Coronary Artery (RCA). Further, as the representative values, for example, the display controlling function 353 displays the smallest FFR values for each of the blood vessel branches. Further, for example, as the representative values, the display controlling function 353 displays the FFR value exhibited in a position away from the tip end by a predetermined distance (e.g., the position 20 mm away from the tip end) with respect to each of the blood vessel branches. Further, for example, as the representative values, the display controlling function 353 displays the FFR value exhibited in such a position that has a blood vessel diameter equal to a predetermine value (e.g., a diameter of 2.5 mm) and is closest to the distal end with respect to each of the blood vessel branches. In that situation, the calculating function 352 calculates the FFR values in those positions. The example of the display in FIG. 5A is merely an example, and possible embodiments are not limited to this example. For instance, a representative value may be displayed not only for each of the three blood vessel branches mentioned above, but for each of all the blood vessel branches included in the coronary artery.

Further, as for the display of the representative values, besides the configuration where the representative value is displayed for each of the blood vessel branches of the coronary artery, another arrangement is also acceptable in which, for example, a representative value is displayed for all the blood vessel branches. In one example, the display controlling function 353 causes the display 340 to display, as a representative value, the smallest FFR value among the FFR values of all the blood vessel branches of the coronary artery. In other words, the display controlling function 353 causes the display 340 to display the smallest value among the FFR values calculated by the calculating function 352. In that situation, the display controlling function 353 may cause the display 340 to display the representative value together with information identifying the blood vessel (e.g., the name such as LAD, LCX, or the like). Alternatively, the display controlling function 353 may cause only the FFR value to be displayed, without the information identifying the blood vessel. With any of these arrangements, the medical doctor is able to immediately recognize the smallest FFR value among all the blood vessel branches and to easily determine specifics of treatments performed in the future.

Alternatively, the display controlling function 353 may display, as a representative value, an average of FFR values exhibited in the blood vessel branches, each in a predetermined position. For example, the display controlling function 353 calculates an average of the FFR values exhibited in the blood vessel branches each in the position 20 mm away from the tip end thereof and causes the display 340 to display the calculated average value. Alternatively, the display controlling function 353 may calculate, with respect to each of the blood vessel branches, an average of FFR values in a number of points between the position 20 mm away and the position 30 mm away from the tip end thereof and may cause the display 340 to display the calculated average value.

Further, the display controlling function 353 is also capable of displaying a representative value for each of predetermined regions in the blood vessel. For example, as illustrated in FIG. 5B, the display controlling function 353 causes the display 340 to display a representative FFR value corresponding to each of the segments (1 to 15) of a coronary artery defined by the American Heart Association (AHA). In this situation, the representative value for each of the segments may be, for example, the smallest FFR value in each of the segments or an FFR value exhibited on the distal-side end of each of the segments. In that situation, the calculating function 352 divides regions in the blood vessel branches of the coronary artery into AHA segments and calculates FFR values in a number of positions in each of the segments resulting from the dividing. The display controlling function 353 extracts the representative FFR value calculated for each of the segments by the calculating function 352 and causes the display 340 to display the extracted representative values.

Figure 5C:
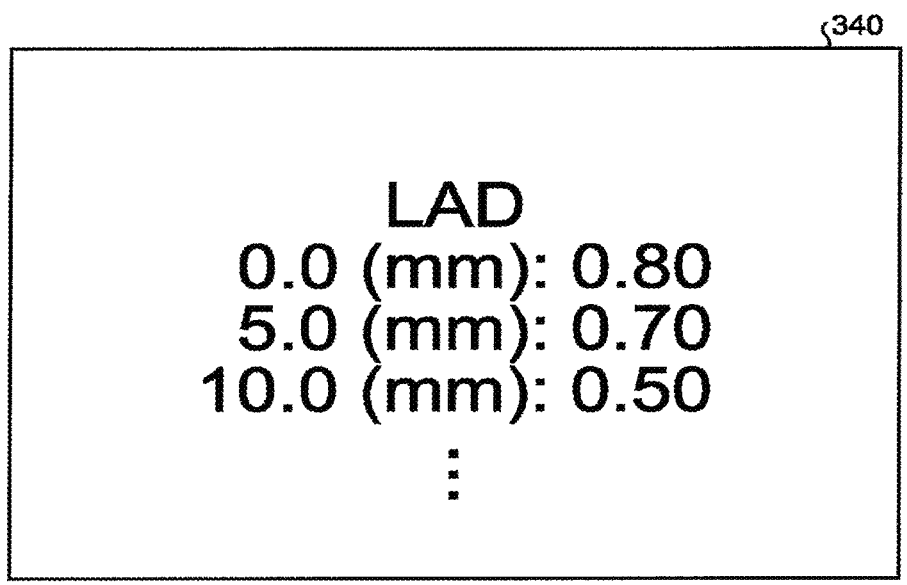
FIG. 5C is a drawing illustrating yet another example of the display of FFR values realized by the display controlling function according to the first embodiment.

Further, the display controlling function 353 is capable of displaying, as a representative value, an FFR value for each of the sections of the blood vessel defined by a predetermined distance. For example, as illustrated in FIG. 5C, the display controlling function 353 displays, with respect to the LAD, an FFR value for each of the sections positioned at intervals of "5 mm" from the branching start part. The example illustrated in FIG. 5C is merely an example, and possible embodiments are not limited to this example. In other words, the display controlling function 353 is able to display an FFR value for each of the sections defined by a predetermined distance with respect to any other blood vessel branches. Further, the distance used for displaying the FFR values may arbitrarily be set.

Figure 5D:
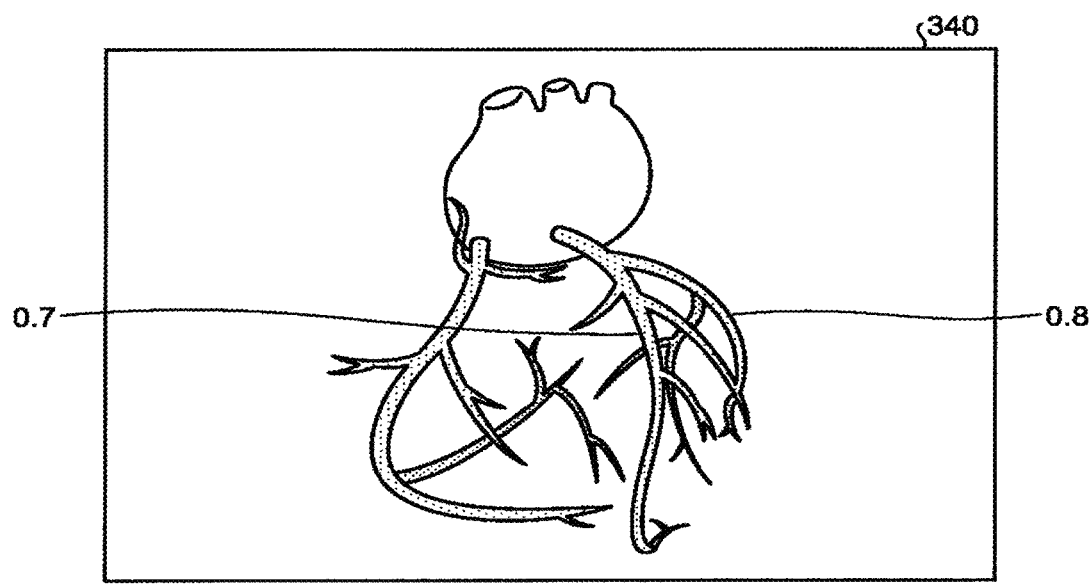
FIG. 5D is a drawing illustrating yet another example of the display of FFR values realized by the display controlling function according to the first embodiment.

Further, the display controlling function 353 is also capable of indicating the FFR values calculated by the calculating function 352 in a schematic diagram illustrating anatomical characteristics of the blood vessel and displaying the schematic diagram together with the FFR values in a predetermined display region. For example, as illustrated in FIG. 5D, the display controlling function 353 causes the display 340 to display certain display information in which representative FFR values are indicated in a textbook-like model image (e.g., an anatomical atlas or the like) illustrating anatomical characteristics. In one example, the display controlling function 353 causes the display 340 to display a piece of display information indicating a representative value for each of the blood vessels illustrated in a schematic diagram.

Some examples of the display of the FFR values realized by the display controlling function 353 have thus been explained. It is possible to use any of the examples of the display explained above in combination, as appropriate. For example, when displaying the smallest FFR value for each of the blood vessel branches or each of the segments, the display controlling function 353 may display, together with each value, the distance from the position exhibiting the smallest value to the branching start part.

As explained above, the display controlling function 353 according to the first embodiment is capable of displaying the representative FFR values, without involving a position designating process that uses a blood vessel display image or a display of a three-dimensional model (a color map) based on an image. In this situation, after the representative values are displayed, by receiving a designating operation through the input interface 330, the medical information processing apparatus 300 is able to change, in response to the designating operation, the locations from which the FFR values displayed on the display 340 are obtained. More specifically, the input interface 330 receives the designating operation to designate a position in the blood vessel rendered in a display image that is generated by using the CT image data and is displayed in a display region different from the predetermined display region. The calculating function 352 calculates an FFR value exhibited in the position designated by the designating operation received by the input interface 330. The display controlling function 353 causes the predetermined display region to display the FFR value exhibited in the position designated by the designating operation.

Figure 6:
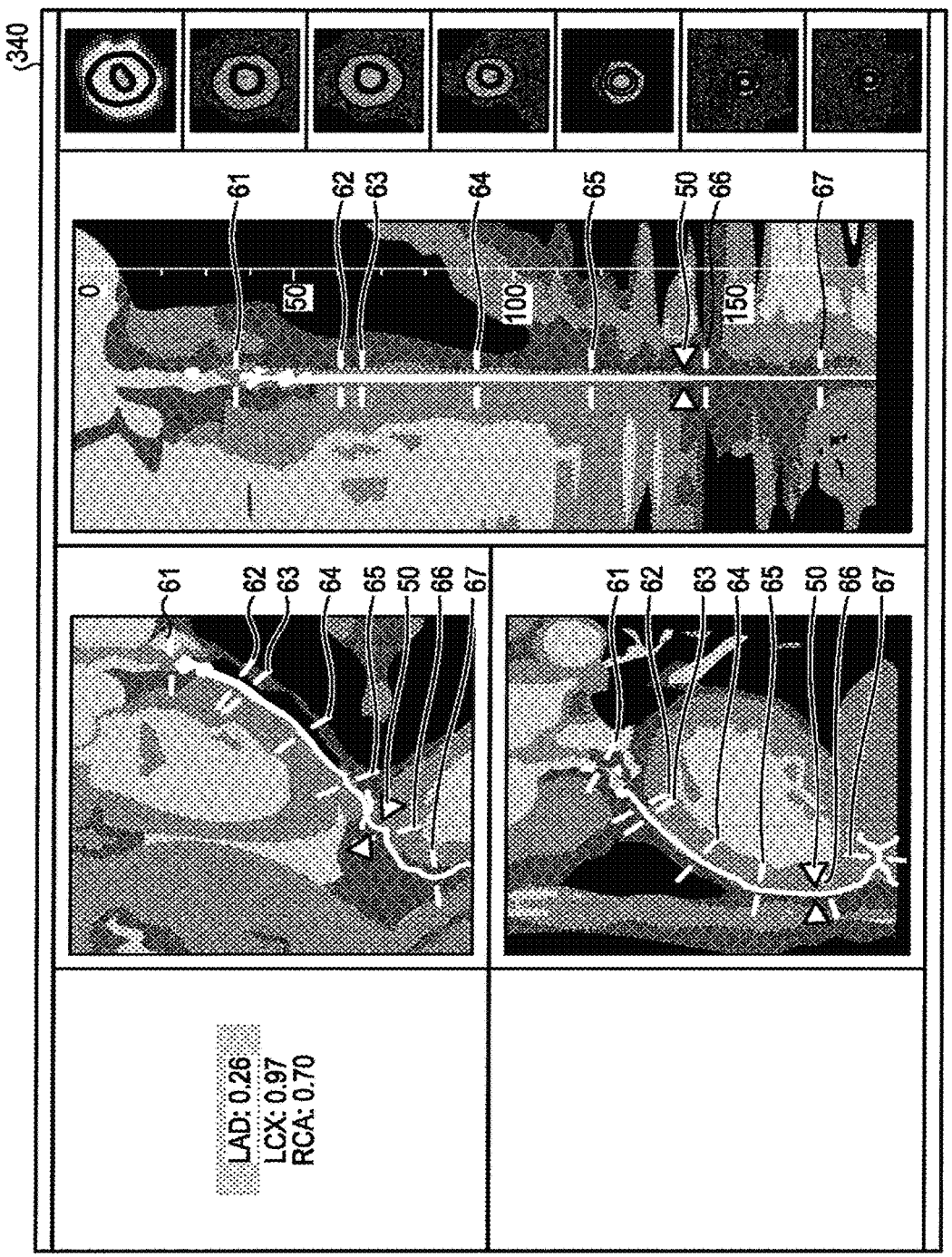
FIG. 6 is a drawing for explaining display control exercised by the display controlling function according to the first embodiment.

FIG. 6 is a drawing for explaining display control exercised by the display controlling function 353 according to the first embodiment. For example, as illustrated in FIG. 6, the display controlling function 353 causes the display 340 to display cross-sectional images of the blood vessel, separately from the representative FFR values of the blood vessel branches. In the present example, the images illustrated in FIG. 6 are a CPR image, an SPR image, and short-axis cross-sectional images (images of cross-sections that are each orthogonal to the central line) that are generated from the CT image data by the controlling function 351. For example, by using the CT image data on which the fluid analysis was performed, the controlling function 351 generates the CPR image, the SPR image, and the short-axis cross-sectional images of the LAD. The short-axis cross-sectional images illustrated on the far right of FIG. 6 are cross-sections taken in positions 61 to 67 indicated in the CPR image and the SPR image.

For example, as illustrated in FIG. 6, the display controlling function 353 displays a marker 50 arranged with the LAD in the CPR image and the LAD in the SPR image. The input interface 330 is configured to receive a moving operation to move the marker 50. After that, the display controlling function 353 causes the FFR values corresponding to the positions of the marker 50 to be displayed in the upper left section of the display 340. In one example, the display controlling function 353 arranges the marker 50 to be positioned at the distal-side end of the target region when starting the display and causes the display 340 to display the FFR value exhibited at the distal-side end of the target region. After that, the input interface 330 receives a moving operation to move the marker 50 along the LAD. The display controlling function 353 then displays the FFR values corresponding to the positions of the marker 50 moved via the input interface 330, in conjunction with the moving of the marker 50.

Although FIG. 6 illustrates the example in which the marker 50 is arranged in the cross-sectional images, possible embodiments are not limited to this example. For instance, the marker 50 may be arranged in a volume rendering image. Further, the display controlling function 353 is also capable of displaying the short-axis cross-sectional image corresponding to the position of the marker 50 in a highlighted manner (e.g., in a slightly larger size).

The examples of the display of the FFR values realized by the display controlling function 353 according to the first embodiment have thus been explained. In this situation, the medical information processing apparatus 300 according to the first embodiment is capable of outputting the representative FFR values (text information) calculated in correspondence with the blood vessel branches or the segments to an electronic medical record. For example, the display controlling function 353 may output a representative value of each of the blood vessel branches to the electronic medical record so as to be kept in correspondence with the blood vessel branch or may output a representative value of each of the segments to the electronic medical record so as to be kept in correspondence with the segment. Further, for example, the display controlling function 353 is also able to output an image indicating the FFR value corresponding to the position of the marker 50 to the electronic medical record and to further output a clinical image having the marker 50 arranged therein to the electronic medical record while being kept in correspondence with the image indicating the FFR value. Furthermore, when an FFR value has been selected from the electronic medical record, the display controlling function 353 displays a clinical image such as a cross-sectional image or a volume rendering image, together with a marker specifying the position from which the selected FFR value was calculated. With these arrangements, the medical doctor is able, at first, to perform a diagnosing process by referring to the representative FFR values. It is therefore possible to improve the efficiency of the diagnosing process.

Figure 7:
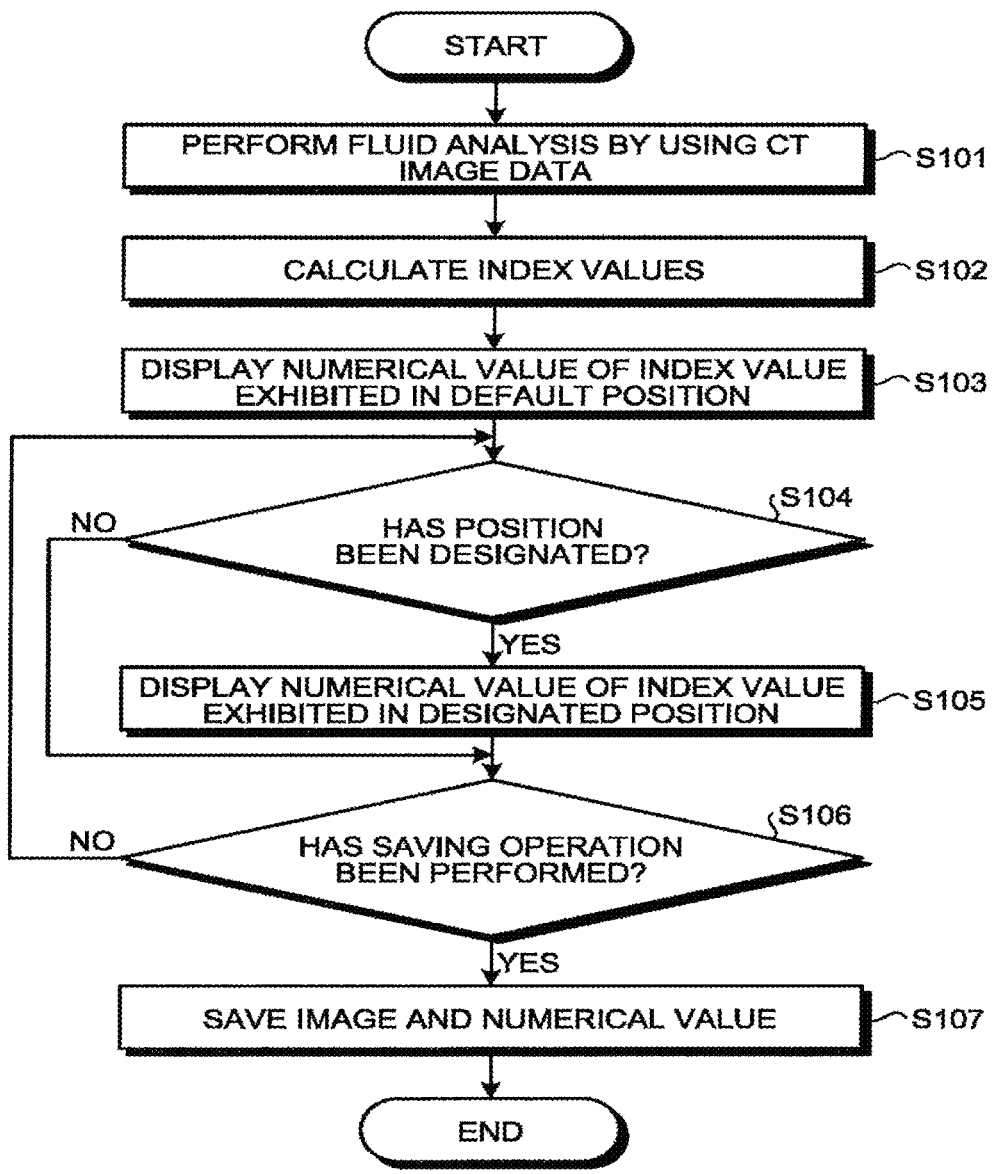
FIG. 7 is a flowchart illustrating a processing procedure performed by the medical information processing apparatus according to the first embodiment.

Next, a procedure in a process performed by the medical information processing apparatus 300 according to the first embodiment will be explained. FIG. 7 is a flowchart illustrating the processing procedure performed by the medical information processing apparatus 300 according to the first embodiment. In the present example, steps S101 and S102 in FIG. 7 are realized as a result of, for example, the processing circuitry 350 invoking and executing a computer program (hereinafter, "program") corresponding to the calculating function 352 from the storage 320. Further, steps S103 through S107 are realized as a result of, for example, the processing circuitry 350 invoking and executing a program corresponding to the display controlling function 353 from the storage 320.

In the medical information processing apparatus 300 according to the present embodiment, at first, the processing circuitry 350 performs a fluid analysis by using the acquired CT image data (step S101) and calculates index values (e.g., FFR values) related to a blood flow (step S102). After that, the processing circuitry 350 displays a numerical value of the index value exhibited in a default position (step S103). In this situation, for example, the processing circuitry 350 displays the FFR value exhibited at the distal-side end of the target region as the index value in the default position. Subsequently, the processing circuitry 350 judges whether or not a position in the blood vessel has been designated via the input interface 330 (step S104).

When a position has been designated (step S104: Yes), the processing circuitry 350 causes the display 340 to display the numerical value of the index value exhibited in the designated position (step S105) and judges whether or not a saving operation has been performed (step S106). On the contrary, when no position has been designated at step S104 (step S104: No), the processing circuitry 350 judges whether or not a saving operation has been performed (step S106).

When the saving operation has been performed (step S106: Yes), the processing circuitry 350 saves the display image and the numerical value (step S107). For example, the processing circuitry 350 saves the image and the numerical value into the storage 320 so as to be kept in correspondence with each other and also outputs the numerical value to the electronic medical record. In this situation, until the saving operation is performed (step S106: No), the processing circuitry 350 continues to judge whether or not the process of designating a position has been performed.

As explained above, according to the first embodiment, the calculating function 352 is configured to calculate the representative values of the index related to the blood flow in the blood vessel by performing the fluid analysis using the image data rendering the blood vessel. The display controlling function 353 causes the display 340 to display the representative values in the predetermined region thereof used for displaying the representative values. Accordingly, the medical information processing apparatus 300 according to the first embodiment is able to immediately present the medical doctor with the representative FFR values and thus makes it possible to improve the efficiency of the diagnosing process.

Further, in the first embodiment, the calculating function 352 is configured to calculate, as the representative value, as least one selected from between: the index related to the blood flow and exhibited at the distal-side end of the target region subject to the fluid analysis within the blood vessel; and the smallest value of the index related to the blood flow in the blood vessel. Accordingly, the medical information processing apparatus 300 according to the first embodiment is able to automatically present the index values suitable for diagnosing processes and thus makes it possible to further improve the efficiency of the diagnosing processes.

Further, according to the first embodiment, the calculating function 352 is configured to calculate the representative value for each of the blood vessels rendered in the CT image data. Accordingly, the medical information processing apparatus 300 according to the first embodiment makes it possible to perform a diagnosing process on the blood vessels rendered in the CT image data in comprehensive manner.

Further, according to the first embodiment, the calculating function 352 is configured to calculate the representative value with respect to either each of the predetermined regions or each of the sections defined by the predetermined distance in the blood vessel. Accordingly, the medical information processing apparatus 300 according to the first embodiment makes it possible to present the indices corresponding to the various conditions.

Further, according to the first embodiment, the display controlling function 353 is configured to indicate the representative value in the schematic diagram illustrating the anatomical characteristics of the blood vessel and to cause the schematic diagram together with the representative value to be displayed in the predetermined display region. Accordingly, the medical information processing apparatus 300 according to the first embodiment makes it possible to visually recognize the positions in which the index values were calculated.

Further, according to the first embodiment, the input interface 330 is configured to receive the designating operation to designate the position with respect to the blood vessel rendered in the display image that is generated by using the CT image data and is displayed in the display region different from the predetermined display region. The calculating function 352 is configured to calculate the index related to the blood flow in the position designated by the designating operation received by the input interface 330. The display controlling function 353 causes the predetermined display region to display the value of the index related to the blood flow in the position designated by the designating operation. Accordingly, the medical information processing apparatus 300 according to the first embodiment makes it possible to easily display the index value exhibited in any arbitrary region.

Second Embodiment

In the first embodiment above, the example is explained in which the FFR values are automatically displayed on the display 340. In a second embodiment, an example will be explained in which the display is switched between FFR values and a clinical image by performing a simple operation. The configuration of the medical information processing apparatus 300 according to the second embodiment is basically the same as the configuration of the medical information processing apparatus 300 illustrated in FIG. 2. Accordingly, the explanations in the following sections focus on differences from the medical information processing apparatus 300 according to the first embodiment. Some of the constituent elements that play the same roles as those of the constituent elements in FIG. 2 will be referred to by using the same reference characters, and detailed explanations thereof will be omitted.

The input interface 330 according to the second embodiment is configured to receive a predetermined input operation performed in a display region of the display 340. For example, the input interface 330 receives an operation to click on a display region in an arbitrary position or an operation to click on a clinical image displayed in a display region.

The display controlling function 353 according to the second embodiment switches the display information in the display region of the display 340 into the representative value of the index related to the blood flow, in response to the input interface 330 receiving the predetermined input operation. More specifically, the display controlling function 353 switches between the display of the clinical image and the display of the FFR values in response to the input interface 330 receiving the input operation.

FIG. 8A is a drawing illustrating an example of the display switching process performed by the display controlling function 353 according to the second embodiment. For example, as illustrated in the top section of FIG. 8A, the display controlling function 353 causes the display 340 to display clinical images (a volume rendering image, a CPR image, and a SPR image) generated from the CT image data. In this situation, when the input interface 330 has received a predetermined input operation performed in the display region, the display controlling function 353 switches the display on the display 340 into a display of only "FFR: 0.73", as illustrated in the bottom section of FIG. 8A.

In this situation, the display controlling function 353 changes the FFR value after the switching process into a corresponding FFR value, in accordance with the position of the input operation received by the input interface 330. For example, when the input interface 330 has received a click operation performed in a position unrelated to the blood vessels within any of the clinical images, the display controlling function 353 switches the display into either a value exhibited in a default position set in advance or a default FFR value. In this situation, the default FFR value may be, for example, any of the representative FFR values explained in the first embodiment, such as an FFR value exhibited in the distal-side end of the target region or the smallest FFR value in the blood vessel.

In contrast, when the input interface 330 has received a click operation performed on a blood vessel rendered in a clinical image, the display controlling function 353 switches the display into a display of an FFR value exhibited in the position in which the click operation was received. In this situation, the display controlling function 353 is able to display the FFR value after the switching process, by adding thereto a note or a symbol indicating whether the FFR value is the default FFR value or the FFR value exhibited in the designated position. For example, the display controlling function 353 is able to add such a note or a symbol to the indication "FFR: 0.73" illustrated in the bottom section of FIG. 8A.

Further, the display controlling function 353 according to the second embodiment switches the display information in the display region of the display 340 into a chart of the index related to the blood flow, in response to the input interface 330 receiving the predetermined input operation. More specifically, the display controlling function 353 switches between the display of the clinical images and the display of the FFR chart with respect to the targeted blood vessel, in response to the input interface 330 receiving the input operation.

FIG. 8B is a drawing illustrating another example of the display switching process performed by the display controlling function 353 according to the second embodiment. For example, as illustrated in the top section of FIG. 8B, the display controlling function 353 causes the display 340 to display clinical images (a volume rendering image, a CPR image, and an SPR image) generated from the CT image data. In this situation, when the input interface 330 has received the predetermined input operation performed in the display region, the display controlling function 353 switches the display on the display 340 into a display of an FFR chart, as illustrated in the bottom section of FIG. 8B. In the present example, in the chart in FIG. 8B, the vertical axis expresses FFR values, whereas the horizontal axis expresses positions in the blood vessel.

For example, when the input interface 330 has received a click operation, the display controlling function 353 switches the display information into the FFR chart of the blood vessel rendered in the clinical images, as illustrated in the bottom section of FIG. 8B. In this situation, the chart displayed by the display controlling function 353 has an additional line drawn therein for the purpose of assessing the FFR value. For example, as illustrated in the bottom section of FIG. 8B, the display controlling function 353 displays the chart in which the additional line is drawn at the FFR value "0.8".

Further, as illustrated in FIG. 8B, the display controlling function 353 is also capable of having an FFR value displayed together with the chart. In this situation, the FFR value displayed together with the chart may be, for example, an FFR value exhibited at the distal-side end of the target region or the smallest FFR value in the blood vessel. Although FIG. 8B illustrates the example in which the switching process is performed between the clinical images and the chart with respect to one blood vessel, possible embodiments are not limited to this example. For instance, the switching process may be performed between clinical images and charts with respect to a plurality of blood vessels.

Further, the medical information processing apparatus 300 according to the second embodiment is capable of saving the display screens before and after the switching process as images. In that situation, for example, the input interface 330 further receives a saving operation to save the display information displayed on the display 340. After that, when the input interface 330 has received the saving operation, the display controlling function 353 outputs the pieces of display information displayed by the display 340 before and after the switching process, each as a piece of image information. For example, when the input interface 330 has received the saving operation, the display controlling function 353 captures the screen illustrated in the top section and the screen illustrated in the bottom section of FIG. 8A and stores the captured screens into the storage 320 so as to be kept in correspondence with each other. Similarly, when the input interface 330 has received the saving operation, the display controlling function 353 captures the screen illustrated in the top section and the screen illustrated in the bottom section of FIG. 8B and stores the captured screens into the storage 320 so as to be kept in correspondence with each other. Alternatively, instead of the operation of capturing and saving the two images, the clinical images in the top section may be saved as the captured images, while the FFR value in the bottom section may be saved as text data.

Next, a procedure in a process performed by the medical information processing apparatus 300 according to the second embodiment will be explained. FIG. 9 is a flowchart illustrating the processing procedure performed by the medical information processing apparatus 300 according to the second embodiment. In the present example, steps S201 and S202 in FIG. 9 are realized as a result of, for example, the processing circuitry 350 invoking and executing a program corresponding to the calculating function 352 from the storage 320. Further, steps S203 through S207 are realized as a result of, for example, the processing circuitry 350 invoking and executing a program corresponding to the display controlling function 353 from the storage 320.

In the medical information processing apparatus 300 according to the present embodiment, at first, the processing circuitry 350 performs a fluid analysis by using the acquired CT image data (step S201) and calculates index values (e.g., FFR values) related to a blood flow (step S202). After that, the processing circuitry 350 displays images generated from the CT image data (step S203). Further, the processing circuitry 350 judges whether or not an operation has been received via the input interface 330 (step S204).

When the operation has been received (step S204: Yes), the processing circuitry 350 causes the display 340 to display only the numerical value of the index value exhibited in the position corresponding to the operation (step S205) and judges whether or not a saving operation has been performed (step S206). On the contrary, at step S204, until the operation is received (step S204: No), the processing circuitry 350 continues to judge whether or not the operation has been received.

When the saving operation has been performed (step S206: Yes), the processing circuitry 350 saves a captured image of the clinical images and a captured image of the numerical value (step S207). For example, the processing circuitry 350 saves the captured image of the clinical images and the captured image of the numerical value into the storage 320 so as to be kept in correspondence with each other. In this situation, until the saving operation is performed (step S206: No), the processing circuitry 350 continues to judge whether or not the saving operation has been performed.

As explained above, according to the second embodiment, the input interface 330 is configured to receive the predetermined input operation performed in the display region of the display 340. The display controlling function 353 is configured to switch the display information in the display region of the display 340 into the representative value of the index related to the blood flow, in response to the input interface 330 receiving the predetermined input operation. Further, the display controlling function 353 is configured to switch the display information in the display region of the display 340 into the chart of the index related to the blood flow, in response to the input interface 330 receiving the predetermined input operation. Accordingly, the medical information processing apparatus 300 according to the second embodiment makes it possible to display the FFR value and the chart in an easy-to-see manner, by receiving the simple operation.

As explained above, according to the second embodiment, the input interface 330 is configured to further receive the saving operation to save the display information displayed on the display 340. The display controlling function 353 is configured to output the pieces of display information displayed by the display 340 before and after the switching process, each as a piece of image information, when the input interface 330 has received the saving operation. Accordingly, the medical information processing apparatus 300 according to the second embodiment makes it possible to save the clinical images, the FFR value, and the chart so as to be easily read from the storage.

Third Embodiment

In the first and the second embodiments described above, the example is explained in which the FFR value is displayed on the display 340. In a third embodiment, an example will be explained in which supplementary information is further displayed in addition to the FFR value. The configuration of the medical information processing apparatus 300 according to the third embodiment is basically the same as the configuration of the medical information processing apparatus 300 illustrated in FIG. 2. Accordingly, the explanations in the following sections focus on differences from the medical information processing apparatus 300 according to the first and the second embodiments. Some of the constituent elements that play the same roles as those of the constituent elements in FIG. 2 will be referred to by using the same reference characters, and detailed explanations thereof will be omitted.

The calculating function 352 according to the third embodiment is configured to calculate an index value of a blood vessel with respect to each of different positions in the blood vessel and to further calculate at least one selected from between: an index value difference obtained by calculating the difference in the calculated index value between two or more positions; and a stenosis percentage value with respect to each of different positions in the blood vessel. For example, the calculating function 352 calculates at least one selected from between: a ΔFFR value obtained by calculating the difference in the FFR value of the blood vessel between two or more positions; and a percentage diameter stenosis (% DS) value.

Figure 10A:
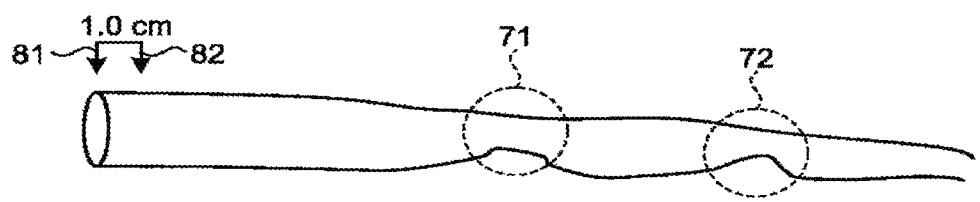
FIG. 10A is a drawing for explaining an example of a calculation of ΔFFR values performed by a calculating function according to a third embodiment.
Figure 10B:
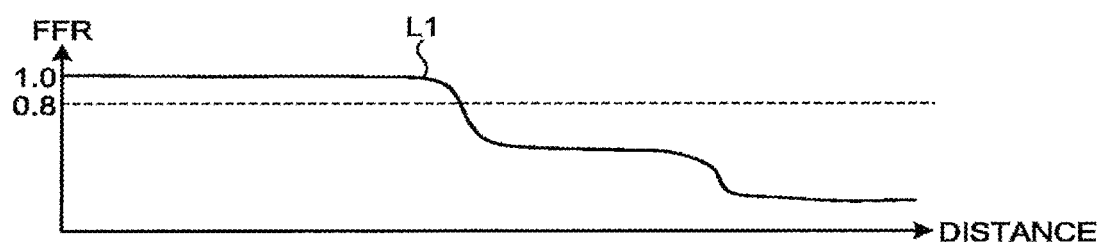
FIG. 10B is a drawing for explaining another example of the calculation of ΔFFR values performed by the calculating function according to the third embodiment.
Figure 10C:
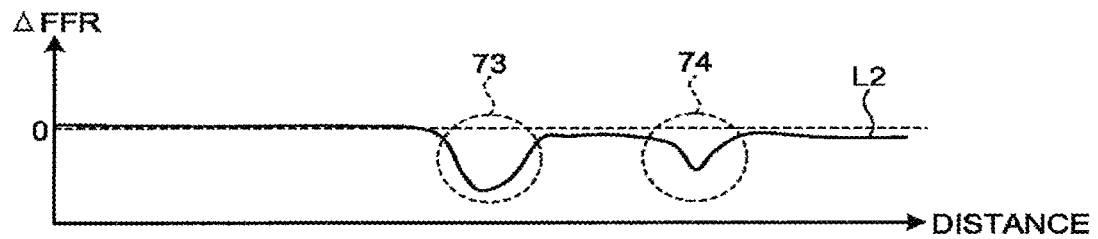
FIG. 10C is a drawing for explaining yet another example of the calculation of ΔFFR values performed by the calculating function according to the third embodiment.

FIGS. 10A to 10C are drawings for explaining examples of a calculation of ΔFFR values performed by the calculating function 352 according to the third embodiment. In the present examples, FIG. 10A illustrates a blood vessel of which the ΔFFR values are to be calculated and a calculation section for the ΔFFR values of the blood vessel. FIG. 10B illustrates a chart of FFR values of the blood vessel illustrated in FIG. 10A. FIG. 10C is a chart illustrating an example of the ΔFFR values calculated by the calculating function 352.

For example, as illustrated in FIG. 10A, the calculating function 352 sets a calculation section length "1.0 cm" used for calculating the ΔFFR values with respect to the blood vessel of which the ΔFFR values are to be calculated. In this situation, the calculation section length is the length used for determining the positions between which the difference in the FFR value is to be calculated. For example, when the calculation section length "1.0 cm" illustrated in FIG. 10A is used, the difference is calculated between the FFR value in the position indicated by an arrow 81 and the FFR value in the position indicated by an arrow 82, with respect to the blood vessel. In other words, the calculating function 352 calculates the difference between each pair of positions by moving the calculation section illustrated in FIG. 10A along the blood vessel by the predetermined distance at a time.

In one example, at first, the calculating function 352 calculates the difference (a ΔFFR value) between the FFR value in the position indicated by the arrow 81 and the FFR value in the position indicated by the arrow 82, which are the positions according to the calculation section illustrated in FIG. 10A. After that, the calculating function 352 moves the calculation section by "1 mm" along the blood vessel (toward the right hand side in the drawing) and further calculates the difference (another ΔFFR value) between the FFR value in the position indicated by the arrow 81 and the FFR value in the position indicated by the arrow 81 with respect to the positions after the move. Similarly, by moving the calculation section along the blood vessel by "1 mm" at a time, the calculating function 352 sequentially calculates ΔFFR values between pairs of positions.

With this arrangement, the calculating function 352 is able to calculate the ΔFFR values corresponding to the various positions in the blood vessel (expressed with distances from the branching start part), as indicated by a curve L2 in FIG. 10C. The length of the calculation sections used for calculating the ΔFFR values may arbitrarily be set. For example, the calculating function 352 is able to extract a stenosis or a plague from the CT image data and to set the calculation section length in accordance with the size of the extracted stenosis or plaque. In one example, the calculating function 352 may set the calculation section length substantially equal to the length of the stenosis or the plaque measured in the long-axis direction of the blood vessel.

The ΔFFR values calculated by the calculating function 352 in this manner may be used for, for example, evaluating a plurality of stenoses as illustrated in FIG. 10A. For example, when the blood vessel has a stenosis 71 and a stenosis 72 as illustrated in FIG. 10A, an FFR chart of the blood vessel exhibits that the FFR value drops in the positions of the stenoses as indicated by the curve L1 in FIG. 10B. If the stenosis 71 and the stenosis 72 were evaluated by using only the FFR chart in FIG. 10B, it would be difficult to understand which stenosis has a larger impact on the blood flow.

In contrast, when the viewer refers to the ΔFFR values calculated by the calculating function 352, the viewer is able to understand that, of the two fluctuation positions 73 and 74 where the ΔFFR value significantly changes, a larger impact is made on the blood flow in the fluctuation position 73 where the change in the ΔFFR value is larger (where the FFR value drops more drastically). In other words, the viewer is able to understand that the stenosis 71 corresponding to the fluctuation position 73 has a larger impact on the blood flow and has a higher priority for a treatment.

Further, the calculating function 352 according to the third embodiment is configured to calculate a percentage diameter stenosis value on the basis of the inside diameter of the blood vessel. For example, by using the CT image data, the calculating function 352 calculates the diameter of the lumen of the blood vessel with respect to each of different positions in the blood vessel and further calculates a percentage diameter stenosis (% DS) value by using the calculated diameters of the lumen in the different positions.

Figure 11B:
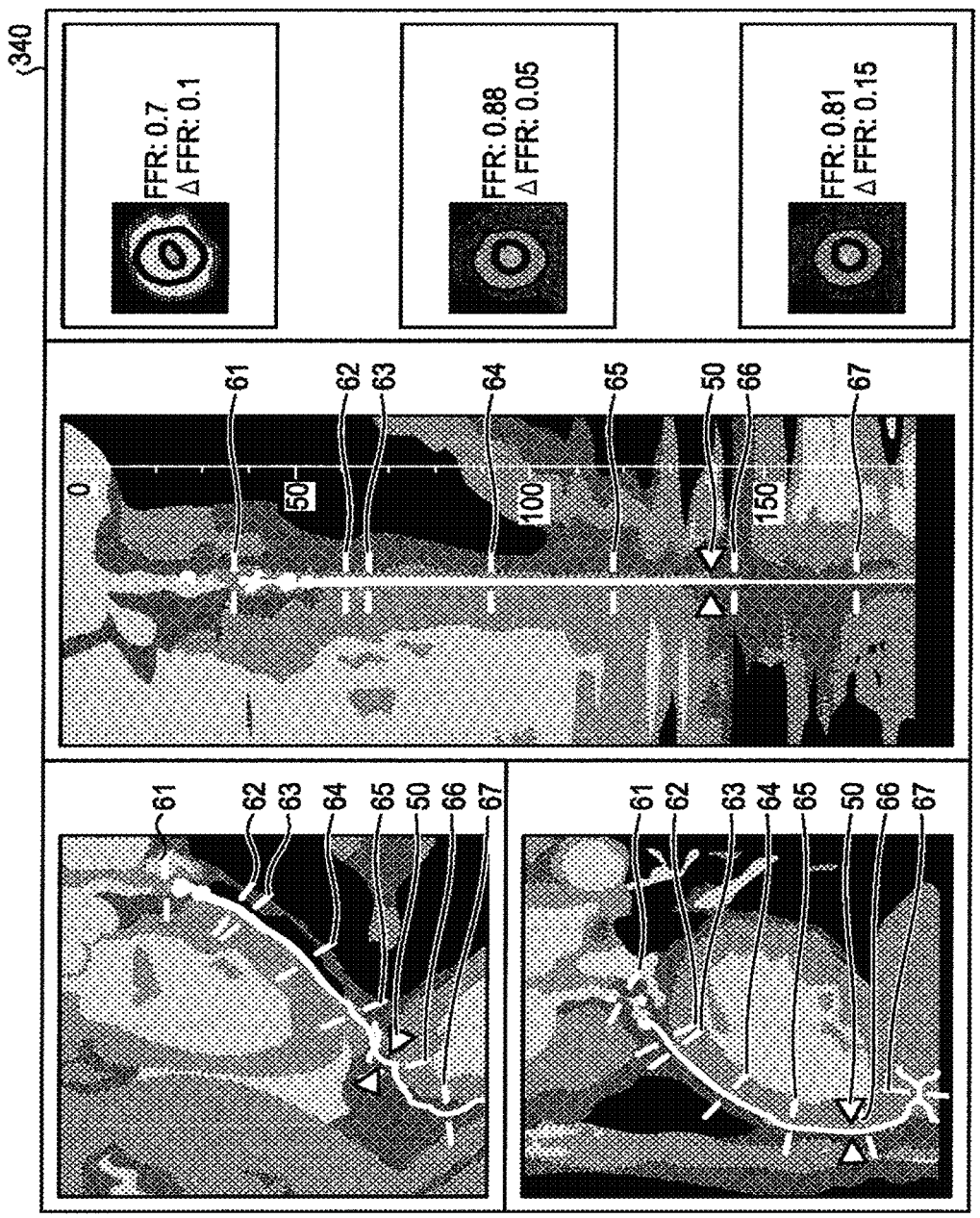
FIG. 11B is a drawing illustrating another example of the display of supplementary information realized by the display controlling function according to the third embodiment.

The display controlling function 353 according to the third embodiment causes a display region of the display 340 to further display at least one selected from between the ΔFFR values and the percentage diameter stenosis value. FIGS. 11A to 11C are drawings illustrating examples of displays of supplementary information realized by the display controlling function 353 according to the third embodiment. For example, when the calculating function 352 has performed the fluid analysis and calculated the ΔFFR values, the display controlling function 353 displays, as illustrated in FIG. 11A, a representative FFR value together with a ΔFFR value exhibited in the position where the representative value was calculated, with respect to each of the blood vessel branches. In this situation, the displayed representative FFR values may be any of the various types of representative values, similarly to the first embodiment. In other words, the display controlling function 353 determines the representative FFR values to be displayed, displays the representative FFR values, and also displays the corresponding ΔFFR values that are kept in correspondence with the FFR values.

Further, for example, as illustrated in FIG. 11B, the display controlling function 353 displays FFR values and ΔFFR values together with short-axis cross-sectional images of the blood vessel. For example, as illustrated in FIG. 11B, the display controlling function 353 displays "FFR: 0.7; ΔFFR: 0.1" together with the short-axis cross-sectional image corresponding to a position 61 in the blood vessel, "FFR: 0.88; ΔFFR: 0.05" together with the short-axis cross-sectional image corresponding to a position 62, and "FFR: 0.81; ΔFFR: 0.15" together with the short-axis cross-sectional image corresponding to a position 63.

Further, for example, as illustrated in FIG. 11C, the display controlling function 353 displays FFR values and percentage diameter stenosis values together with short-axis cross-sectional images of the blood vessel. For example, as illustrated in FIG. 11C, the display controlling function 353 displays "FFR: 0.7; % DS: 20" together with the short-axis cross-sectional image corresponding to the position 61 in the blood vessel, "FFR: 0.88; % DS: 80" together with the short-axis cross-sectional image corresponding to the position 62, and "FFR: 0.81; % DS: 50" together with the short-axis cross-sectional image corresponding to the position 63.

Further, the display controlling function 353 is also able to display an FFR value and the supplementary information (a ΔFFR value and/or a percentage diameter stenosis value) together with a short-axis cross-sectional image in the position indicated by the marker 50. In that situation, in response to an operation to move the marker 50 realized via the input interface 330, the display controlling function 353 changes the display of the short-axis cross-sectional image, the FFR value, and the supplementary information in conjunction with the moving operation.

Figure 12:
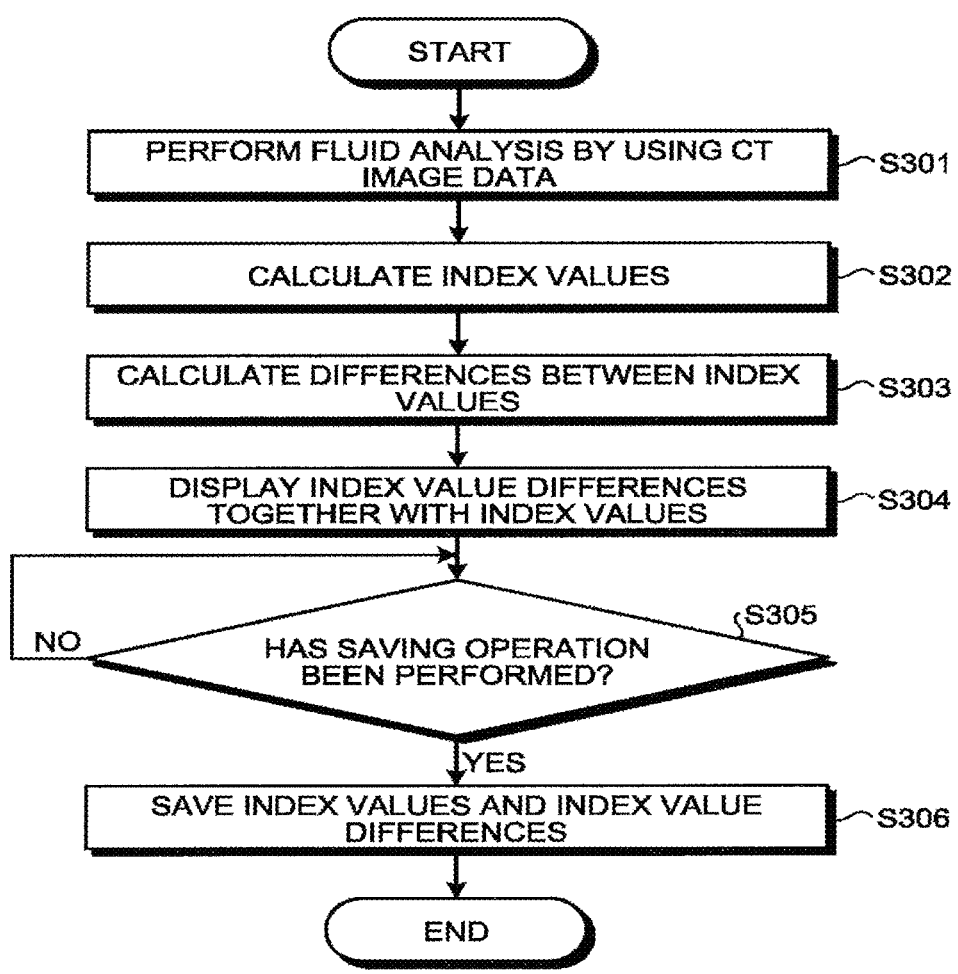
FIG. 12 is a flowchart illustrating a processing procedure performed by a medical information processing apparatus according to the third embodiment.

Next, a procedure in a process performed by the medical information processing apparatus 300 according to the third embodiment will be explained. FIG. 12 is a flowchart illustrating the processing procedure performed by the medical information processing apparatus 300 according to the third embodiment. In the present example, steps S301 through S303 in FIG. 12 are realized as a result of, for example, the processing circuitry 350 invoking and executing a program corresponding to the calculating function 352 from the storage 320. Further, steps S304 through S306 are realized as a result of, for example, the processing circuitry 350 invoking and executing a program corresponding to the display controlling function 353 from the storage 320.

In the medical information processing apparatus 300 according to the present embodiment, at first, the processing circuitry 350 performs a fluid analysis by using the acquired CT image data (step S301) and calculates index values (e.g., FFR values) related to a blood flow (step S302). Further, the processing circuitry 350 calculates differences (the ΔFFR values) between the index values along the blood vessel (step S303). After that, the processing circuitry 350 displays the index value differences together with the index values (step S304). Subsequently, the processing circuitry 350 judges whether or not a saving operation has been received via the input interface 330 (step S305).

When the saving operation has been performed (step S305: Yes), the processing circuitry 350 saves the index values and the index value differences (step S306). In this situation, until the saving operation is performed (step S305: No), the processing circuitry 350 continues to judge whether or not the saving operation has been performed.

As explained above, according to the third embodiment, the calculating function 352 is configured to calculate the FFR value of the blood vessel for each of the different positions in the blood vessel and to further calculate at least one selected from between: the ΔFFR values obtained by calculating the differences in the calculated FFR value between the pairs of positions; and the percentage diameter stenosis values corresponding to the different positions in the blood vessel. Further, the display controlling function 353 causes the display region of the display 340 to further display at least one selected from between the ΔFFR values and the percentage diameter stenosis values. Consequently, the medical information processing apparatus 300 according to the third embodiment is able to further display the supplementary information and thus makes it possible to further improve the efficiency of the diagnosing processes.

Fourth Embodiment

In the first to the third embodiments above, the examples are explained in which the display 340 is caused to display the arbitrary clinical images. In a fourth embodiment, an example will be explained in which clinical images to be displayed are changed in accordance with results of the fluid analysis. The configuration of the medical information processing apparatus 300 according to the fourth embodiment is basically the same as the configuration of the medical information processing apparatus 300 illustrated in FIG. 2. Accordingly, the explanations in the following sections focus on differences from the medical information processing apparatus 300 according to the first to the third embodiments. Some of the constituent elements that play the same roles as those of the constituent elements in FIG. 2 will be referred to by using the same reference characters, and detailed explanations thereof will be omitted.

The controlling function 351 according to the fourth embodiment is configured to generate a display image corresponding to a calculation result obtained by the calculating function 352. More specifically, the controlling function 351 is configured to generate a clinical image indicating, in a straight-on position, either the position exhibiting the smallest FFR value or the position exhibiting the largest ΔFFR value. For example, the controlling function 351 generates a volume rendering image indicating, in a straight-on position, a blood vessel exhibiting the smallest FFR value or a blood vessel exhibiting the largest ΔFFR value. Further, the controlling function 351 generates a volume rendering image indicating, at the center of the display 340, a position exhibiting the smallest FFR value or a position exhibiting the largest ΔFFR value, with respect to a predetermined blood vessel. Further, the controlling function 351 generates a CPR image and/or an SPR image of either the blood vessel exhibiting the smallest FFR value or the blood vessel exhibiting the largest ΔFFR value.

Figure 13:
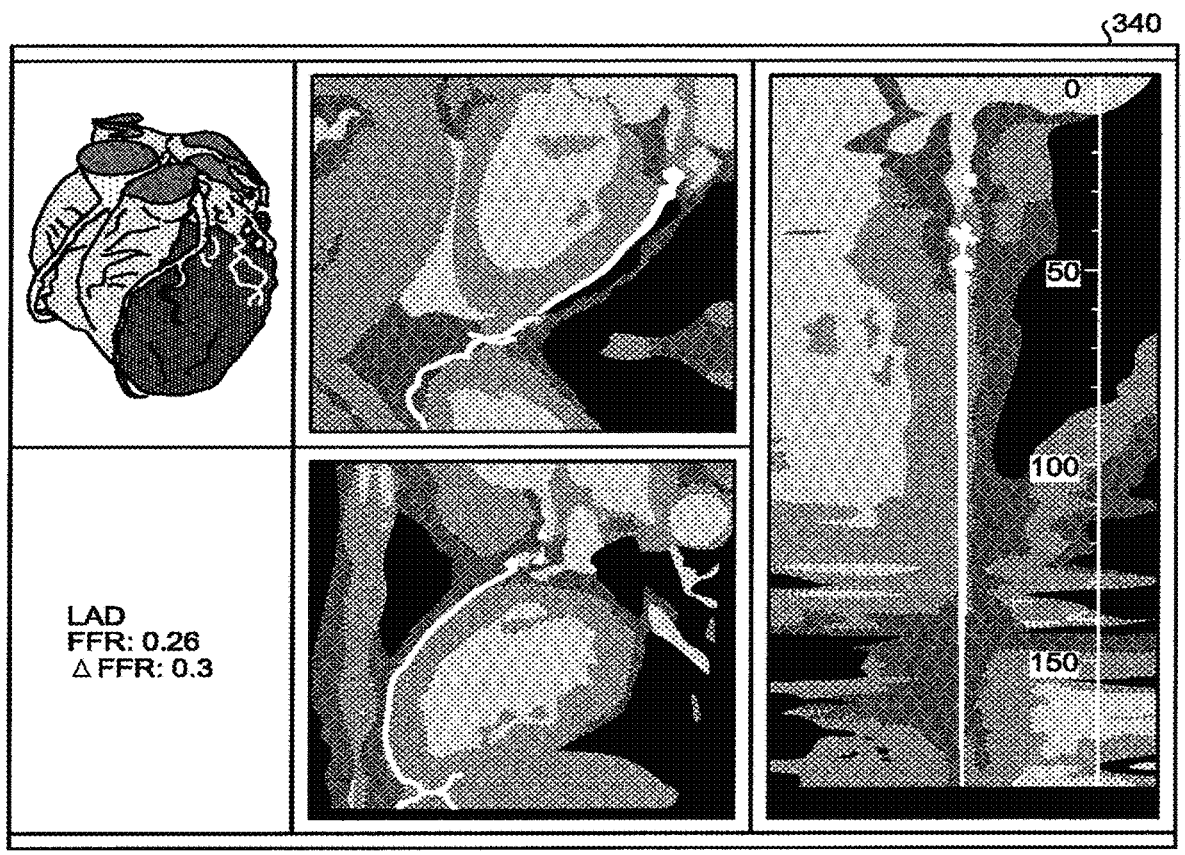
FIG. 13 is a drawing illustrating an example of a display of clinical images realized by a display controlling function according to a fourth embodiment.

The display controlling function 353 according to the fourth embodiment causes a display region of the display 340 to display any of the clinical images generated by the controlling function 351. FIG. 13 is a drawing illustrating an example of a display of the clinical images realized by the display controlling function 353 according to the fourth embodiment. For example, when the calculating function 352 has performed the fluid analysis, the display controlling function 353 causes the display 340 to display, as illustrated in FIG. 13, a volume rendering image that provides a view of the blood vessel LAD from a straight-on position, as well as a CPR image and an SPR image of the LAD, the blood vessel LAD exhibiting the smallest FFR value calculated by the calculating function 352. In this situation, as illustrated in FIG. 13, the display controlling function 353 causes a display region different from the display region of the clinical images to display an FFR value "0.26" and a ΔFFR value "0.3", together with the clinical images.

Figure 14:
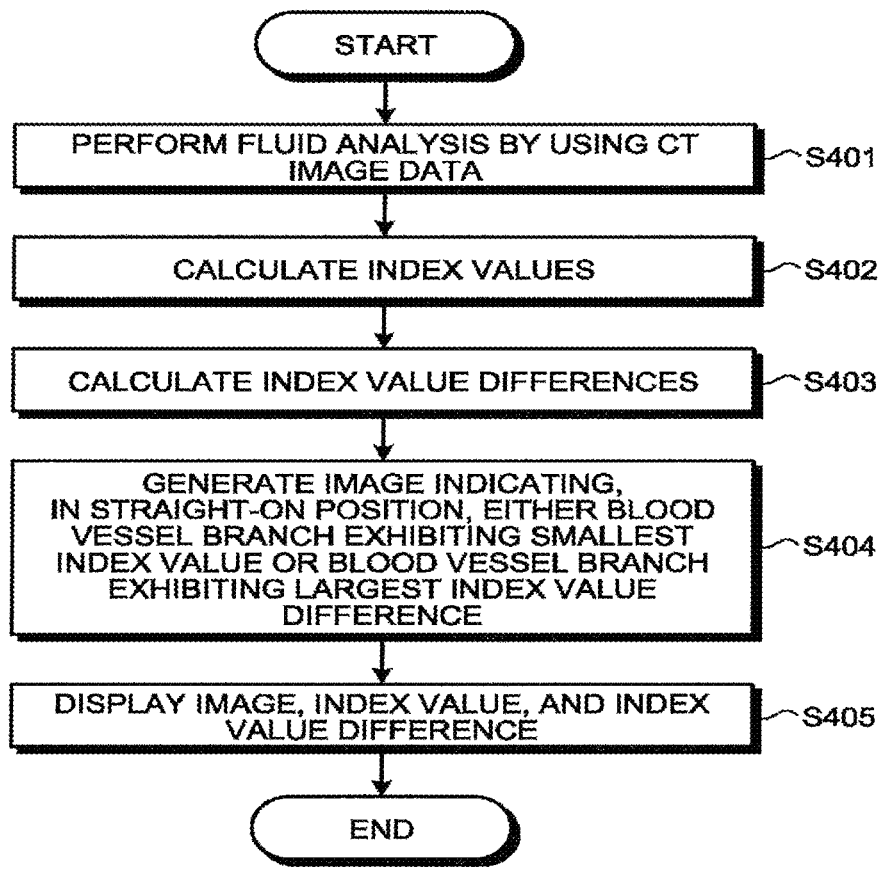
FIG. 14 is a flowchart illustrating a processing procedure performed by a medical information processing apparatus according to the fourth embodiment.

Next, a procedure in a process performed by the medical information processing apparatus 300 according to the fourth embodiment will be explained. FIG. 14 is a flowchart illustrating the processing procedure performed by the medical information processing apparatus 300 according to the fourth embodiment. In the present example, steps S401 through S403 in FIG. 14 are realized as a result of, for example, the processing circuitry 350 invoking and executing a program corresponding to the calculating function 352 from the storage 320. Further, step S404 is realized as a result of, for example, the processing circuitry 350 invoking and executing a program corresponding to the controlling function 351 from the storage 320. Further, step S405 is realized as a result of, for example, the processing circuitry 350 invoking and executing a program corresponding to the display controlling function 353 from the storage 320.

In the medical information processing apparatus 300 according to the present embodiment, at first, the processing circuitry 350 performs a fluid analysis by using the acquired CT image data (step S401) and calculates index values (e.g., FFR values) related to a blood flow (step S402). Further, the processing circuitry 350 calculates index value differences (ΔFFR values) along the blood vessel (step S403). After that, the processing circuitry 350 generates a clinical image indicating, in a straight-on position, either a blood vessel branch exhibiting the smallest index value or a blood vessel branch exhibiting the largest index value difference (step S404). Subsequently, the processing circuitry 350 causes the display 340 to display the clinical image, the index value, and the index value difference (step S405).

As explained above, according to the fourth embodiment, the controlling function 351 is configured to generate the display image corresponding to the calculation results obtained by the calculating function 352. For example, the controlling function 351 is configured to generate at least one selected from between: the display image indicating, in the straight-on position, either the position exhibiting the smallest FFR value in the blood vessel or the position exhibiting the largest ΔFFR value obtained by calculating the differences between the pairs of positions in the blood vessel; and the display image indicating the cross-section taken at either the position exhibiting the smallest FFR value or the position exhibiting the largest ΔFFR value. The display controlling function 353 is configured to cause the display region of the display 340 to display the display image generated by the controlling function 351. Consequently, the medical information processing apparatus 300 according to the fourth embodiment is able to display the clinical image suitable for diagnosing processes and thus make it possible to further improve the efficiency of the diagnosing processes.

Fifth Embodiment

The first to the fourth embodiments have thus been explained. It is, however, possible to carry out the present disclosure in other various forms in addition to those explained in the first to the fourth embodiments.

In the embodiments above, the example is explained in which the FFR values are displayed as an index related to the blood flow. However, possible embodiments are not limited to this example. For instance, it is acceptable to display any other index such as an index related to the flow rate, the flow speed, the pressure, or the like. In that situation, a value used as a representative value is set with respect to each of the indices.

Further, in the embodiments described above, the example is explained in which, as the representative value, the display controlling function 353 displays the index value (e.g., the FFR value) exhibited in the distal-side end of the blood vessel, the smallest FFR value in the blood vessel, or the index value exhibited in a position away from the distal-side end by the predetermined distance (e.g., in the position 20 mm away from the end). However, the examples described above are merely examples. The display controlling function 353 is able to display any of other various types of index values as the representative value.

For example, the display controlling function 353 is able to display, as a representative value, an index value exhibited in such a position where the index value drastically changes. In that situation, with respect to index values exhibited in different positions in the blood vessel, the calculating function 352 sets such a position where a change amount in the index value along the extending direction of the blood vessel exceeds a threshold value, as a position in the blood vessel from which the first value is to be obtained. In other words, the calculating function 352 calculates index value differences between pairs of positions in the blood vessel and sets the index value exhibited in such a position where the calculated difference exceeds the threshold value as a representative value. For example, the calculating function 352 sets the FFR value exhibited in such a position where the abovementioned ΔFFR value exceeds a predetermined threshold value, as a representative value. In this situation, the calculating function 352 may also set the two index values used for calculating the difference as representative values. In one example, the calculating function 352 may set the FFR value exhibited on the branching start part side and the FFR value exhibited on the distal side of the blood vessel, both corresponding to a ΔFFR value exceeding the predetermined threshold value, as representative values. Alternatively, the calculating function 352 may use one selected from between the FFR value exhibited on the branching start part side and the FFR value exhibited on the distal side of the blood vessel, as a representative value. Further, the threshold value compared with the difference may arbitrarily be set and is stored in the storage 320 in advance.

Further, for example, the display controlling function 353 may display the index value exhibited in such a position where the cross-sectional area of the blood vessel drastically changes as a representative value. In that situation, the calculating function 352 analyzes the shape of the blood vessel of the patient and sets such a position where a change amount in the cross-sectional area of the blood vessel along the extending direction of the blood vessel exceeds a threshold value, as a position in the blood vessel from which the first value is to be obtained. In other words, the calculating function 352 calculates the differences in the cross-sectional area between pairs of positions in the blood vessel and further sets the index value exhibited in such a position where the calculated difference exceeds the threshold value, as a representative value. For example, the calculating function 352 may set the FFR value exhibited on the branching start part side and the FFR value exhibited on the distal side of the blood vessel, both corresponding to a cross-sectional area difference exceeding the threshold value, as representative values. Alternatively, the calculating function 352 may use one selected from between the FFR value exhibited on the branching start part side and the FFR value exhibited on the distal side of the blood vessel, as a representative value. Further, the threshold value compared with the difference may arbitrarily be set and is stored in the storage 320 in advance.

Further, for example, the display controlling function 353 is able to display a representative value based on a lesion site included in the blood vessel. In that situation, the calculating function 352 analyzes a blood vessel of the patient and further sets a position on the distal side of the lesion site included in the blood vessel, as a position in the blood vessel from which the first value is to be obtained. For example, the calculating function 352 extracts a stenosis region by analyzing the blood vessel and sets the index value exhibited in a position on the distal side of the extracted stenosis region, as a representative value. In one example, the calculating function 352 sets the FFR value exhibited in the position that is away from the stenosis region on the distal side by a predetermined distance (e.g., 10 mm), as a representative value. When there are two or more stenosis regions, the calculating function 352 sets, for example, the smallest FFR value among the stenosis regions as a representative value.

Further, for example, the calculating function 352 may set an index value exhibited in a position on the distal side of a plaque region in the blood vessel, as a representative value. In that situation, at first, the calculating function 352 detects the position of the plaque region by analyzing the CT image data. In this situation, to detect the plaque region, it is possible to use any of various existing methods. Further, for example, the calculating function 352 sets the FFR value exhibited immediately below the detected plaque region (in a proximate region on the distal side), as a representative value. In the present disclosure, an "immediately below" position denotes a location corresponding to the pertinent site (e.g., a location corresponding to the plaque region) or a position that is away from the pertinent site (e.g., the plaque region) on the distal side by a predetermined distance.

Further, for example, the display controlling function 353 is able to display an index value of which the degree of reliability exceeds a threshold value, as a representative value. In that situation, during the fluid analysis performed on the CT image data, the calculating function 352 calculates the degree of reliability of each of the index values exhibited in different positions in the blood vessel and further sets a representative value from among such index values of which the calculated degrees of reliability each exceed the predetermined threshold value. The threshold value may arbitrarily be set and is stored in the storage 320 in advance. The degree of reliability may be combined with another index. For example, from among such index values of which the calculated degrees of reliability each exceed the predetermined threshold value, a value exhibited at the end on the distal side may be set as a representative value.

Figure 15B:
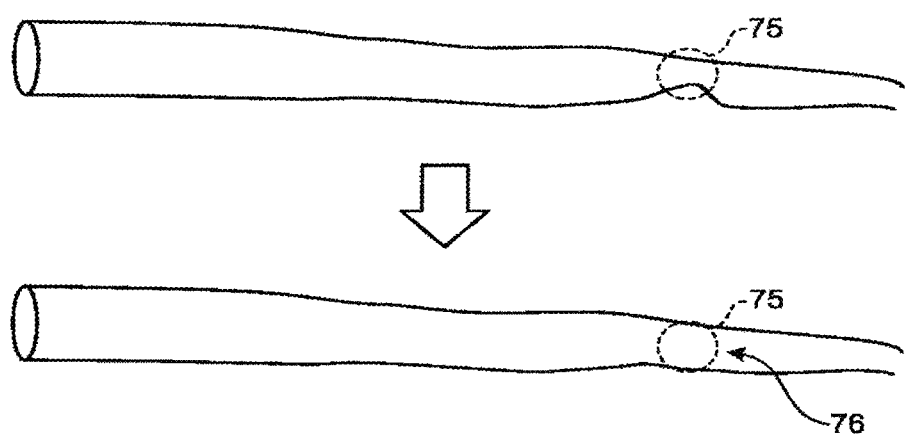
FIG. 15B is a drawing for explaining another example of a representative value according to the fifth embodiment.
Figure 15C:
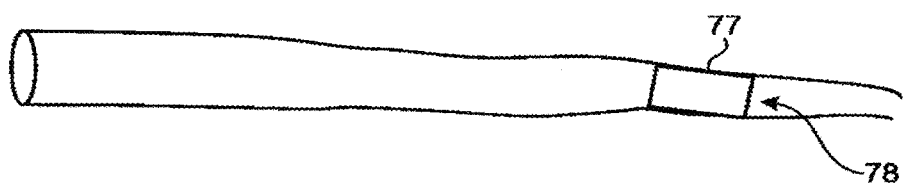
FIG. 15C is a drawing for explaining yet another example of a representative value according to the fifth embodiment.

Further, for example, the display controlling function 353 is able to display an index value exhibited in a position in which the viewer is interested (hereinafter "a position of interest") in the blood vessel, as a representative value. In that situation, the calculating function 352 sets the position of interest in the blood vessel as a position in the blood vessel from which the first value is to be obtained. In this situation, the position of interest is one selected from among the following: a position in the blood vessel included in past information of the patient; a position where the shape was virtually changed by a simulation in a fluid analysis performed on the blood vessel; a position in which a treatment was applied to the blood vessel; and a position designated prior to a treatment applied to the blood vessel. Next, examples of the representative values will be explained, with reference to FIGS. 15A to 15C. FIGS. 15A to 15C are drawings for explaining the examples of the representative values according to a fifth embodiment.

First, an example of the representative value based on past information of the patient will be explained. For example, as illustrated in FIG. 15A, the calculating function 352 sets the same position as a position set in a past report, as a representative value of an index value to be currently displayed. In this situation, the report generated during a medical examination or a diagnosing process is able to store therein an index value exhibited in an arbitrary position designated by the operator. For example, during a medical examination of a patient, an FFR value of a coronary artery is calculated by performing a fluid analysis while using CT image data rendering the coronary artery. Further, when generating a report, the operator manipulates a marker in a three-dimensional model and arranges an FFR value in a desired position to be stored in the report. As a result, as illustrated in the top section of FIG. 15A, the position in the coronary artery desired by the viewer and the FFR value "0.76" exhibited in that position are stored into the past report.

When a fluid analysis is performed again on the same patient as described above, the calculating function 352 reads the past report and identifies which location in the analysis result of the fluid analysis that has just been performed corresponds to the desired position designated in the past report. This identifying process may be completed by performing a position alignment between volume data in which the desired position was designated in the past report and volume data subject to the fluid analysis that has just been performed, so as to match the coordinate systems of the two pieces of volume data. Further, the calculating function 352 sets the FFR value exhibited in the position desired by the viewer included in the past report, as a representative value. In other words, as illustrated in the bottom section of FIG. 15A, the display controlling function 353 displays, as the representative value, the FFR value "0.72" obtained in the fluid analysis that has just been performed and exhibited in the same position as the position stored in the past report. In this situation, within the CT image data that has just been acquired, the calculating function 352 is able to identify the same position as the desired position included in the past report, by using any of various methods.

For example, the calculating function 352 may identify the desired position in the CT image data that has just been acquired, on the basis of the distance between the desired position stored in the past report and the branching start part (or the distal end). In other words, the calculating function 352 identifies the blood vessel branch in which the desired position was designated in the past report and further calculates the distance between the desired position within the identified blood vessel branch and the branching start part (or the distal end). After that, the calculating function 352 identifies the same blood vessel branch within the CT image data that has just been acquired and further identifies such a position in the identified blood vessel branch that is away by the calculated distance, as the same position with the desired position included in the past report. The example of the identifying process described herein is merely an example. The calculating function 352 may identify the position by using any of other various methods. For instance, the calculating function 352 may identify the desired position stored in the past report on the basis of anatomical characteristics of the coronary artery and may identify the same position as the identified position within the CT image data that has just been acquired.

Further, in the embodiment above, the example is explained in which the same position as the position stored in the past report is set as a representative value; however, possible embodiments are not limited to this example. For instance, it is also acceptable to set the same position as the position of an index value currently being displayed by the display 340, as a representative value. In other words, when setting a representative value in a new display image, the calculating function 352 sets the same position as the position of the index value within the display image currently being displayed by the display 340, as the position of the representative value.

Next, an example of a representative value based on a simulation will be explained. For example, as illustrated in FIG. 15B, the calculating function 352 is able to set, as a representative value, an index value exhibited in such a position where the shape was virtually changed during a simulation. For example, the calculating function 352 is able to virtually change the shape of the blood vessel by changing blood vessel shape data in the acquired CT image data and to further perform a fluid analysis on the blood vessel resulting from the shape change. In one example, as illustrated in the bottom section of FIG. 15B, the calculating function 352 changes the shape of the blood vessel in the CT image data into a shape without a stenosis 75 and further performs a fluid analysis on the blood vessel resulting from the shape change. With this arrangement, for example, it is possible to simulate effects of a treatment to be applied to the stenosis 75.

When having performed the simulation described above, the calculating function 352 sets the index value exhibited at the position in the blood vessel where the shape was changed during the simulation, as a representative value. For example, as illustrated in the bottom section of FIG. 15B, the calculating function 352 sets, as a representative value, either the FFR value in a position 76 immediately below the stenosis 75 (in a proximate region on the distal side) or the FFR value exhibited immediately below the position in the blood vessel where the shape was changed.

Next, an example of a representative value based on a position in which a treatment was applied to a blood vessel will be explained. For example, as illustrated in FIG. 15C, the calculating function 352 sets an index value exhibited in a position immediately below a treatment location (a proximate region on the distal side) as a representative value. For example, as illustrated in FIG. 15C, the calculating function 352 sets the FFR value in a position 78 immediately below the position where a stent 77 has been installed, as a representative value. In this situation, besides the positions mentioned above, the calculating function 352 may use, as a position of interest, a position designated prior to a treatment applied to the blood vessel. In other words, the calculating function 352 sets the index value exhibited in the position designated by the operator prior to the treatment, as a representative value.

Further, in the embodiments described above, the example is explained in which the controlling function 351 generates the display image indicating, in the straight-on position, the position exhibiting the smallest FFR value or the position exhibiting the largest ΔFFR value; however, possible embodiments are not limited to this example. For instance, the controlling function 351 may generate a display image indicating, in a straight-on position, a position of interest in the blood vessel. In that situation, for example, the controlling function 351 generates the display image indicating, in the straight-on position, the abovementioned position of interest (e.g., a position in the blood vessel included in past information of the patient, a position where the shape was virtually changed by a simulation in a fluid analysis performed on the blood vessel, a position in which a treatment was applied to the blood vessel, or a position designated prior to a treatment applied to the blood vessel).

Figure 16A:
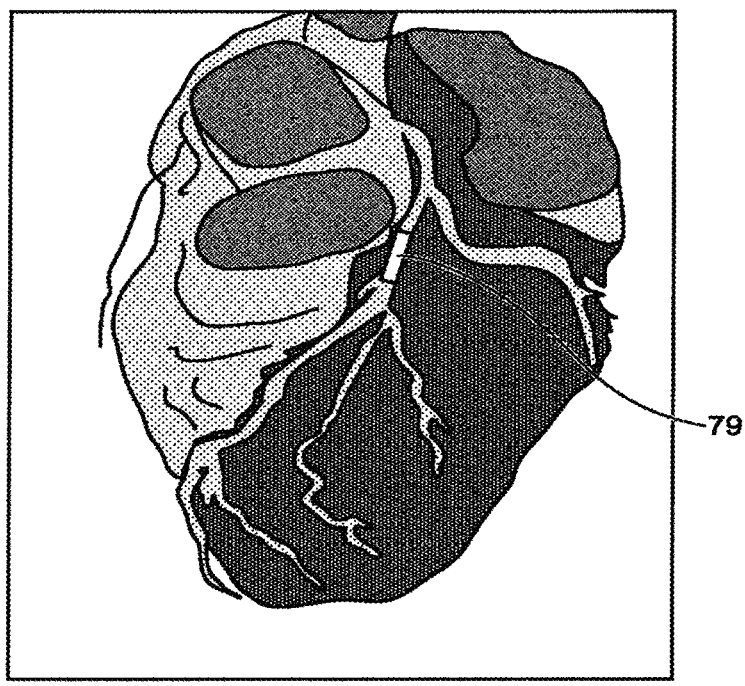
FIG. 16A is a drawing illustrating an example of a display image according to the fifth embodiment.

FIG. 16A is a drawing illustrating an example of the display image according to the fifth embodiment. With reference to FIG. 16A, an example using a volume rendering image will be explained; however, possible embodiments are not limited to this example. A three-dimensional model or a surface rendering image may be used as the display image. For example, as illustrated in FIG. 16A, the controlling function 351 generates a display image indicating, in a straight-on position, the position in which a stent 79 has been installed. In other words, the display controlling function 353 is able to cause the display 340 to display the display image indicating the stent 79 in the straight-on position and also indicating an index value exhibited immediately below the stent 79 as a representative value. As a result, the operator is able to immediately view the index value exhibited in the position of interest.

Figure 16B:
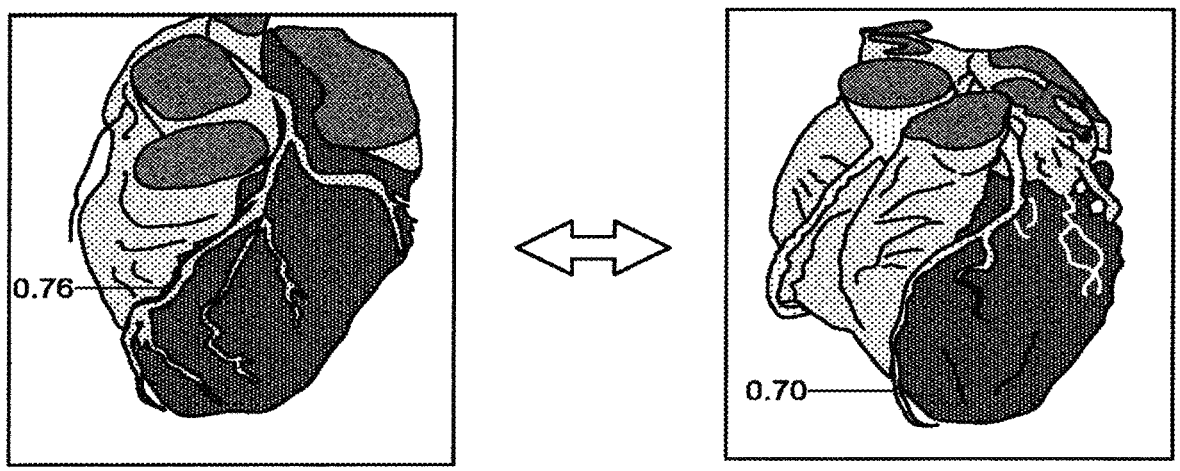
FIG. 16B is a drawing illustrating another example of a display image according to the fifth embodiment.

In this situation, a display image such as that illustrated in FIG. 16A may arbitrarily be rotated in response to an operation performed by the operator. In that situation, the calculating function 352 is able to select a position from which a representative value is to be obtained, in accordance with the orientation of the blood vessel rendered in the display image. FIG. 16B is a drawing illustrating an example of a display image according to the fifth embodiment. With reference to FIG. 16B, an example using a volume rendering image will be explained; however, possible embodiments are not limited to this example. A three-dimensional model or a surface rendering image may be used as the display image. For example, as illustrated in FIG. 16B, the calculating function 352 sets an index value of the blood vessel rendered in a straight-on position in the display image as a representative value. In other words, as illustrated in FIG. 16B, the calculating function 352 switches the representative value from "0.76" to "0.70" or from "0.70" to "0.76", depending on the orientation of the display image. In this situation, as the representative value of the blood vessel rendered in the straight-on position, an arbitrary one of the various types of representative values explained above may be set.

Further, in the embodiments above, the examples are explained in which the index value of the blood vessel is displayed; however, possible embodiments are not limited to these examples. For instance, the index value does not necessarily have to be displayed, depending on the position in the blood vessel. In other words, the display controlling function 353 arranges such an index value that is exhibited in a predetermined site of the blood vessel to be in a non-display state. In this situation, the predetermined site of the blood vessel includes a plaque region, a bypass region, a bridge region, a calcified region, or an image artifact region of the blood vessel.

Figure 17:
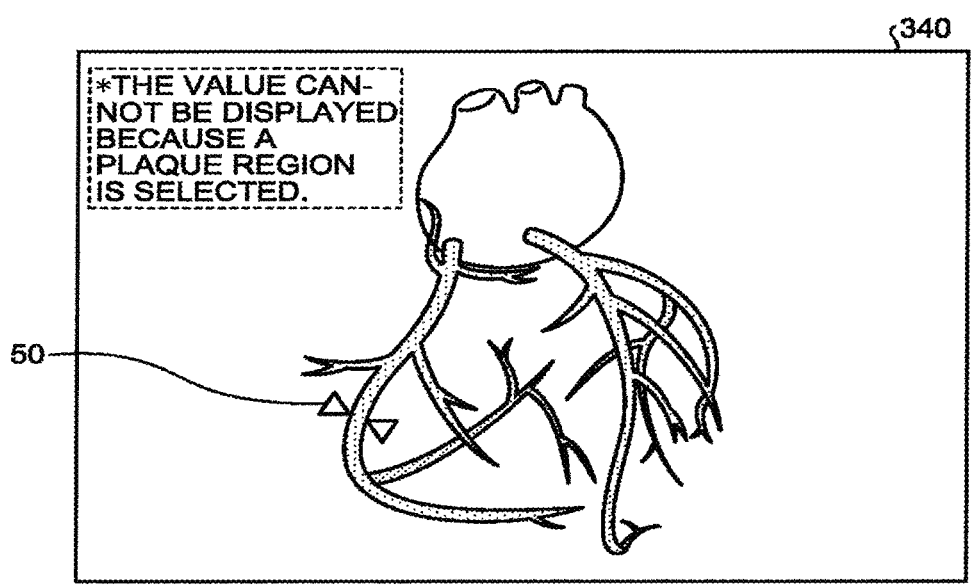
FIG. 17 is a drawing illustrating an example of a display according to the fifth embodiment.

For example, with respect to the CT image data, the display controlling function 353 arranges the FFR values in plaque regions, bypass regions, bridge regions, calcified regions, and image artifact regions to be in a non-display state. In other words, the display controlling function 353 arranges the index value to be in a non-display state, with respect to such a region where it is impossible to calculate an index value or such a region where the degree of reliability of the calculated index value is low. FIG. 17 is a drawing illustrating an example of a display according to the fifth embodiment.

For example, let us discuss a situation where, as illustrated in FIG. 17, the display controlling function 353 arranges the marker 50 to be displayed in a display image and has received a position designating operation as a result of the operator performing an operation to move the marker 50. In that situation, when the marker 50 is positioned in one of the abovementioned predetermined sites, the display controlling function 353 arranges the index value exhibited in the position designated by the marker 50 to be in a non-display state. In this situation, the display controlling function 353 may cause the display 340 to display a note indicating that the index value is in a non-display state. For example, as illustrated in FIG. 17, the display controlling function 353 causes the display 340 to display a note reading "*The value cannot be displayed because a plaque region is selected".

In the above example, the situation is explained in which the index value is in the non-display state even when the marker 50 is placed in the predetermined site within the display image; however, possible embodiments are not limited to this example. For instance, another arrangement is also acceptable where placing the marker 50 is impossible. In other words, the display controlling function 353 may exercise control so as not to display the marker 50 in the predetermined site within the display image.

Further, it is possible to arbitrarily set the size and the color of the numerical values and the text explained in the embodiment above. For example, when a plurality of FFR values are displayed in a display image, the sizes and/or the colors of the numerals may be varied depending on the FFR values.

Further, in the embodiments above, the example is explained in which the representative values are set according to the index values calculated in the fluid analysis or the positions or the like of the index values; however, possible embodiments are not limited to this example. The representative values may be set by combining one or more other conditions together. For instance, it is also acceptable to set a representative value by taking into consideration a range related to an invasive FFR examination (which may be referred to as a wired FFR examination) in which changes in pressure are measured by using a pressure wire so as to calculate FFR values.

In the abovementioned FFR examination using the fluid analysis, it is possible to measure an FFR value up to an end section of the blood vessel of which it is possible to obtain blood vessel structure information from the CT image data. In contrast, when performing the invasive FFR examination, the measurable distance is limited to such locations where the pressure wire can physically be inserted. Accordingly, it is often the case that a blood vessel position from which a fluid analysis is able to obtain an FFR value is closer to the distal end than a blood vessel position from which an invasive FFR examination is able to obtain an FFR value is. For this reason, when analysis results are compared between an invasive FFR examination and an FFR examination using CT image data, the comparison may be complicated due to the fact that the ranges from which it is possible to obtain values are different between the two examinations. Further, when the image quality of the CT image data in a section near the distal end is low, for example, an FFR value obtained from an FFR analysis using CT image data tends to become low in the section closer to the distal end. Accordingly, there is a high possibility that an examination result may exhibit a false positive. To cope with this situation, the medical information processing apparatus 300 of the present disclosure is configured to estimate, within the CT image data, a distal-end position in which the pressure wire is able to perform a measuring process and to display a fluid analysis result (an index value) exhibited in the estimated position as a representative value. With this arrangement, it is possible to present an examination result having a high level of precision. Details of this process will be explained below.

In the medical information processing apparatus 300 described above, the calculating function 352 calculates the distal-end position within the blood vessel in which the pressure wire is able to measure pressure, on the basis of structure information of the blood vessel and structure information of the pressure wire. More specifically, the calculating function 352 estimates a measurable range supposing that the pressure wire is inserted into the blood vessel rendered in the CT image data to measure the pressure, on the basis of the structure of the blood vessel and the structure of the pressure wire.

For example, as information (parameters) about the structure of the blood vessel, the calculating function 352 obtains "the diameter of the blood vessel", "the curvature of the blood vessel", "the torsion of the blood vessel", "the thickness of the blood vessel wall", and the like, from the blood vessel shape data extracted from the CT image data. Further, as information (parameters) about the structure of the pressure wire, the calculating function 352 obtains "the thickness of the pressure wire", "the largest region of a bend of the pressure wire", "a curvature-stress relationship (an elastic force) of the pressure wire", and the like. Information about structures of pressure wires is stored in the storage 320 in advance, in correspondence with different types of pressure wires.

After that, the calculating function 352 estimates a range in the blood vessel in which the pressure wire is able to measure the pressure, on the basis of the information about the structure of the blood vessel and the information about the structure of the pressure wire that were obtained. For example, a threshold value may be set in advance for each of the pieces of information about the structure of the blood vessel such as "the diameter of the blood vessel", "the curvature of the blood vessel", "the torsion of the blood vessel", and "the thickness of the blood vessel wall", so that the calculating function 352 judges whether the pressure wire is able to perform the measuring process, on the basis of the set threshold values. In one example, the calculating function 352 determines such a position where "the blood vessel diameter" is equal to or smaller than "the thickness of the pressure wire", as a position where the measuring process is impossible. For example, a typical value for "the thickness of the pressure wire" is "0.014 inches", "0.014 inches" is set as the threshold value, in advance.

Similarly, the calculating function 352 judges whether the pressure wire is able to perform the measuring process by comparing each of the pieces of information such as "the curvature of the blood vessel", "the torsion of the blood vessel", and "the thickness of the blood vessel wall", with a threshold value. For example, the calculating function 352 may compare each of the abovementioned four parameters with a threshold value and determine such a position where any one of the parameters exceeds the threshold value as a position where the pressure wire is unable to perform the measuring process.

In this situation, the calculating function 352 is also able to perform the abovementioned judging process in combination with the state of the blood vessel. FFR examinations using a fluid analysis are often performed on a blood vessel in a resting state. In contrast, FFR examinations using a pressure wire are often performed in a stress state achieved by administering adenosine to the patient. Accordingly, the shape of a blood vessel subject to an FFR examination using a pressure wire may be different from the shape of the blood vessel rendered in the CT image data acquired in a resting state and may have a larger blood vessel diameter, for example. To cope with this situation, in order to make judgments while combining these states, the calculating function 352 converts the structure information of the blood vessel obtained from the CT image data into structure information of the blood vessel in a stress state, so as to calculate the distal-end position of the blood vessel in which the pressure wire is able to measure the pressure, on the basis of the structure information of the pressure wire.

For example, the storage 320 is arranged to store therein, in advance, information about how the shape of a blood vessel in a resting state changes when placed in a stress state. Further, the calculating function 352 reads the information about the shape change from the storage 320 and applies the read information to the CT image data. Accordingly, the calculating function 352 changes the shape of the blood vessel rendered in the CT image data into the shape in a stress state and further obtains the abovementioned four parameters from the blood vessel shape data resulting from the shape change. Subsequently, by comparing each of the four obtained parameters with a threshold value, the calculating function 352 judges whether or not the pressure wire is able to perform the measuring process.

Figure 18A:
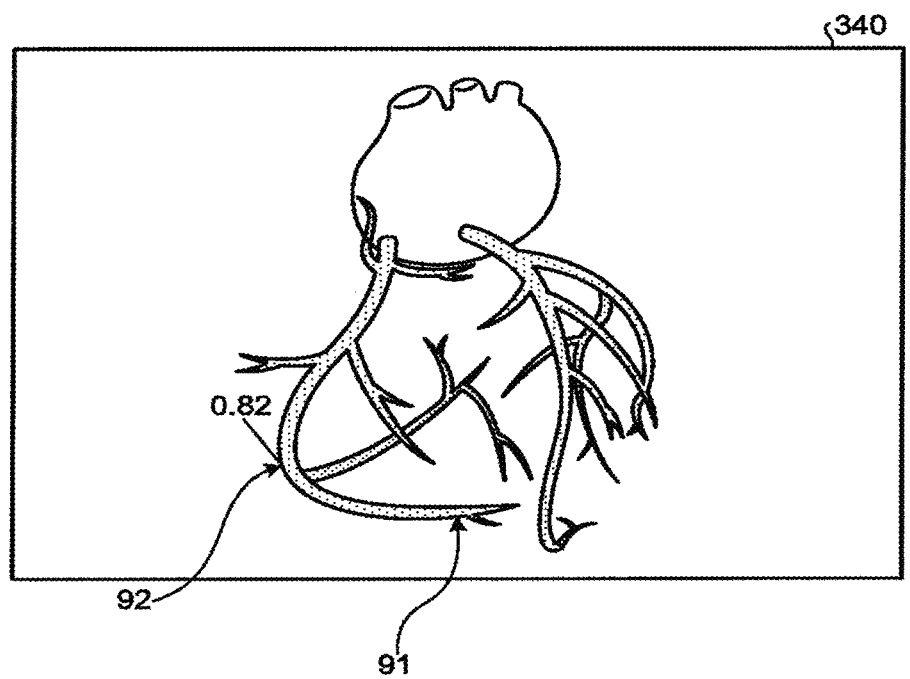
FIG. 18A is a drawing for explaining an example of a representative value according to the fifth embodiment.

In this manner, when having identified the distal-end position of the blood vessel in which the pressure wire is able to measure the pressure, the calculating function 352 sets a result of the fluid analysis exhibited in the identified position as a representative value. FIG. 18A is a drawing for explaining an example of the representative value according to the fifth embodiment. For instance, as illustrated in FIG. 18A, the calculating function 352 identifies a distal end 91 in which an FFR examination using a fluid analysis is able to perform the measuring process and a distal end 92 in which a pressure wire is able to perform the measuring process. After that, with respect to the range in which the FFR examination using the fluid analysis is able to perform the measuring process, the calculating function 352 sets the FFR value "0.82" exhibited in the position of the distal end 92, as a representative value. The display controlling function 353 causes the display 340 to display the representative value "0.82" set by the calculating function 352. As a result, the operator is able to immediately determine a fluid analysis result (e.g., an FFR value) from which position should be regarded as a correct value. Further, as a measuring result of the FFR examination using the fluid analysis, a value exhibited in a position similar to the position measured in the invasive FFR examination is obtained. Accordingly, it is possible to assess, at a glance, the measuring result of the FFR examination using the fluid analysis. It is therefore possible to reduce the burden on the operator when he/she interprets the measuring results.

Figure 18B:
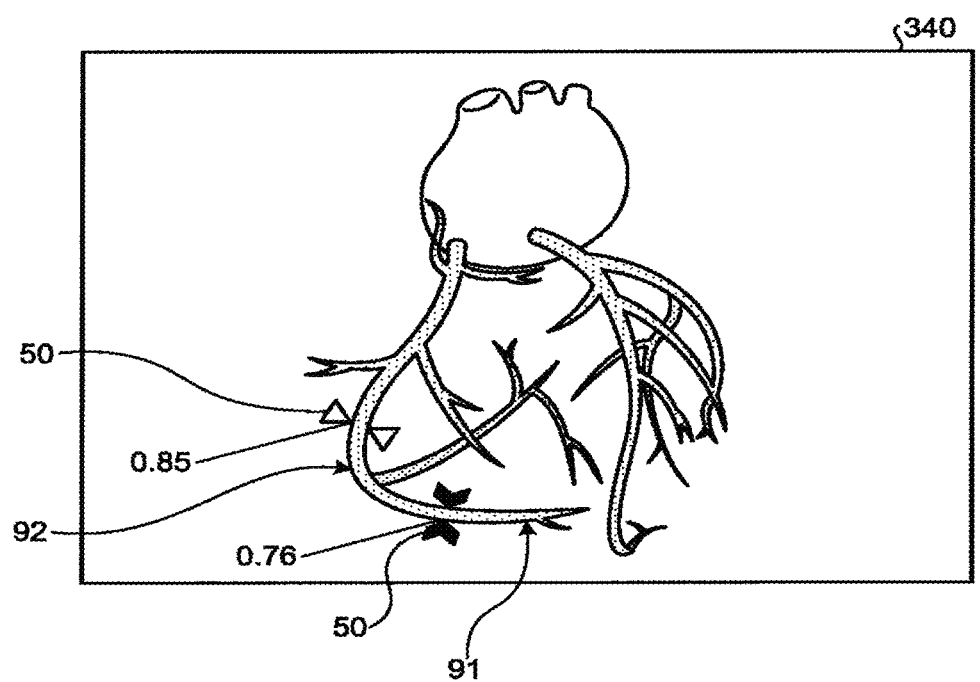
FIG. 18B is a drawing for explaining other examples of representative values according to the fifth embodiment.

Further, even in the situation described above where the range in an invasive FFR examination is taken into consideration, it is also possible to designate the position of an index value to be displayed by using a marker. FIG. 18B is a drawing for explaining other examples of representative values according to the fifth embodiment. Although FIG. 18B illustrates two markers 50 for the sake of convenience in the explanation, one marker 50 is displayed in actuality. For example, as illustrated in FIG. 18B, the display controlling function 353 displays the marker 50 along the blood vessel in the three-dimensional model and receives a designating operation to designate a display position for the index value. After that, the display controlling function 353 causes the index value (e.g., an FFR value) in the position designated by the marker 50 to be displayed in the three-dimensional model.

In this situation, in accordance with the positions of the marker 50, the display controlling function 353 is able to change the display modes of the marker 50 and/or the numerals indicating the index values. For example, as illustrated in FIG. 18B, the display controlling function 353 changes the display modes of the marker 50 used for receiving designating operations and the index values, depending on whether or not the position designated by a designating operation is a position in which the pressure wire is able to measure the pressure. In other words, the display controlling function 353 is able to vary the shape and/or the color of the marker 50 between positions in which the pressure wire is able to perform the measuring process and positions in which the pressure wire is unable to perform the measuring process, but an FFR examination using a fluid analysis is able to perform the measuring process. Also, the display controlling function 353 is able to vary the size and/or the color between the FFR values "0.85" and "0.76".

Further, the display controlling function 353 is also able to display the FFR value measured by the pressure wire and the measuring result obtained by the fluid analysis so as to be arranged side by side. In that situation, for example, provided that an FFR value distribution measured by the pressure wire is available because the pressure wire previously measured or is currently measuring FFR values and that the marker 50 is placed in a position exhibiting one of the FFR values measured by the pressure wire, the display controlling function 353 displays the fluid analysis result (the FFR value) in the position of the marker 50 and the FFR value measured by the pressure wire so as to be arranged side by side.

Various examples of the representative values, the display method, and the image display method have thus been explained. It is possible to use any of the configurations explained in the first to the fifth embodiments in combination as appropriate. In other words, the setting of the representative values and the displaying of the representative values on the display 340 described above may be carried out in any arbitrary combination.

Further, in the embodiments described above, the example is explained in which the medical information processing apparatus 300 performs the various types of processes; however, possible embodiments are not limited to this example. For instance, the X-ray CT apparatus 100 may perform various types of processes. FIG. 19 is a diagram illustrating an exemplary configuration of the X-ray CT apparatus 100 according to the fifth embodiment.

As illustrated in FIG. 19, the X-ray CT apparatus 100 according to the fifth embodiment includes a gantry 10, a table device 20, and a console 30. The gantry 10 is a device configured to radiate X-rays onto a patient P, to detect X-rays that have passed through the patient P, and to output a result of the detection to the console 30. The gantry 10 includes X-ray radiation controlling circuitry 11, an X-ray generating device 12, a detector 13, and data acquiring circuitry (a Data Acquisition System [DAS]) 14, a rotating frame 15, and gantry driving circuitry 16.

The rotating frame 15 is an annular frame configured to support the X-ray generating device 12 and the detector 13 so as to oppose each other while the patient P is interposed therebetween and configured to be rotated by the gantry driving circuitry 16 (explained later) at a high speed on a circular orbit centered on the patient P.

The X-ray radiation controlling circuitry 11 is a device configured, as a high-voltage generating unit, to supply a high voltage to an X-ray tube 12a. The X-ray tube 12a is configured to generate X-rays by using the high voltage supplied thereto from the X-ray radiation controlling circuitry 11. The X-ray radiation controlling circuitry 11 is configured to adjust the X-ray dose radiated onto the patient P, by adjusting the X-ray tube voltage and the X-ray tube current supplied to the X-ray tube 12a, under control of scan controlling circuitry 33 (explained later).

Further, the X-ray radiation controlling circuitry 11 is configured to perform a switching process on a wedge 12b. Further, by adjusting the opening degree of a collimator 12c, the X-ray radiation controlling circuitry 11 is configured to adjust the radiation range (a fan angle and a cone angle) of the X-rays. In the present embodiments, an arrangement is acceptable in which an operator manually switches among a plurality of types of wedges 12b.

The X-ray generating device 12 is a device configured to generate the X-rays and to radiate the generated X-rays onto the patient P. The X-ray generating device 12 includes the X-ray tube 12a, the wedge 12b, and the collimator 12c.

The X-ray tube 12a is a vacuum tube configured to radiate an X-ray beam onto the patient P by using the high voltage supplied thereto by the high-voltage generating unit (not illustrated). The X-ray tube 12a radiates the X-ray beam onto the patient P, as the rotating frame 15 rotates. The X-ray tube 12a is configured to generate the X-ray beam that spreads with the fan angle and the cone angle. For example, under the control of the X-ray radiation controlling circuitry 11, the X-ray tube 12a is capable of continuously emitting X-rays in the entire surrounding of the patient P to realize a full reconstruction process and is capable of continuously emitting X-rays in an emission range (180 degrees+the fan angle) that enables a half reconstruction to realize a half reconstruction process. Further, under the control of the X-ray radiation controlling circuitry 11, the X-ray tube 12a is capable of intermittently emitting X-rays (pulse X-rays) in positions (X-ray tube positions) set in advance. Further, the X-ray radiation controlling circuitry 11 is also capable of modulating the intensities of the X-rays emitted from the X-ray tube 12a. For example, the X-ray radiation controlling circuitry 11 increases the intensities of the X-rays emitted from the X-ray tube 12a in a specific X-ray tube position and decreases the intensities of the X-rays emitted from the X-ray tube 12a in a range other than the specific X-ray tube position.

The wedge 12b is an X-ray filter configured to adjust the X-ray dose of the X-rays emitted from the X-ray tube 12a. More specifically, the wedge 12b is a filter configured to pass and attenuate the X-rays emitted from the X-ray tube 12a, so that the X-rays radiated from the X-ray tube 12a onto the patient P have a predetermined distribution. For example, the wedge 12b is a filter obtained by processing aluminum so as to have a predetermined target angle and a predetermined thickness. The wedge 12b may be referred to as a wedge filter or a bow-tie filter.

The collimator 12c is a slit configured to narrow down the radiation range of the X-rays of which the X-ray dose has been adjusted by the wedge 12b, under the control of the X-ray radiation controlling circuitry 11 (explained later).

The gantry driving circuitry 16 is configured to cause the X-ray generating device 12 and the detector 13 to revolve on the circular orbit centered on the patient P, by driving the rotating frame 15 to rotate.

The detector 13 is a two-dimensional array detector (a planar detector) configured to detect the X-rays that have passed through the patient P. In the detector 13, a plurality of rows of detecting elements are arranged along the Z-axis direction, while each row contains a plurality of X-ray detecting elements corresponding to a plurality of channels. More specifically, the detector 13 includes the X-ray detecting elements that are arranged in a large number of rows (e.g., 320 rows) along the Z-axis direction. For example, the detector 13 is capable of detecting X-rays that have passed through the patient P in a wide range such as a range including the lungs or the heart of the patient P. The Z-axis denotes the axial direction of the rotation center of the rotating frame 15 while the gantry 10 is in a non-tilted state.

The data acquiring circuitry 14 is configured with the DAS and is configured to acquire projection data from X-ray detection data detected by the detector 13. For example, the data acquiring circuitry 14 generates the projection data by performing an amplifying process, an Analog/Digital (A/D) converting process, a sensitivity correcting process among the channels, and/or the like on X-ray intensity distribution data detected by the detector 13 and further transmits the generated projection data to the console 30 (explained later). For example, when X-rays are continuously emitted from the X-ray tube 12a while the rotating frame 15 is rotating, the data acquiring circuitry 14 acquires a group of projection data corresponding to the entire surrounding (corresponding to 360 degrees). Further, the data acquiring circuitry 14 transmits the acquired pieces of projection data to the console 30 (explained later), while keeping the pieces of projection data in correspondence with the X-ray tube positions. The X-ray tube positions serve as information indicating projection directions of the pieces of projection data. Alternatively, the sensitivity correcting process among the channels may be performed by pre-processing circuitry 34 (explained later).

The table device 20 is a device on which the patient P is placed and includes a table driving device 21 and a tabletop 22, as illustrated in FIG. 19. The table driving device 21 is configured to move the patient P into the rotating frame 15 by moving the tabletop 22 in the Z-axis direction. The tabletop 22 is a board on which the patient P is placed. Further, in the present embodiment, the example is explained in which the relative position between the gantry 10 and the tabletop 22 is changed by controlling the tabletop 22; however, possible embodiments are not limited to this example. For example, when the gantry 10 is self-propelled, the relative position between the gantry 10 and the tabletop 22 may be changed by controlling the self-propelled movement of the gantry 10.

For example, the gantry 10 performs a helical scan by which the patient P is helically scanned by causing the rotating frame 15 to rotate while the tabletop 22 is being moved. In another example, the gantry 10 performs a conventional scan by which the patient P is scanned on a circular orbit by causing the rotating frame 15 to rotate, while the position of the patient P is being fixed after the tabletop 22 is moved. In yet another example, the gantry 10 implements a step-and-shoot method by which the conventional scan is performed in multiple scan areas, by moving the position of the tabletop 22 at regular intervals.

The console 30 is a device configured to receive operations performed by the operator on the X-ray CT apparatus 100 and also configured to reconstruct CT image data by using the projection data acquired by the gantry 10. As illustrated in FIG. 19, the console 30 includes an input interface 31, a display 32, the scan controlling circuitry 33, the pre-processing circuitry 34, a storage 35, image reconstructing circuitry 36, and processing circuitry 37.

The input interface 31 includes a mouse, a keyboard, a trackball, a switch, a button, a joystick, and/or the like used by the operator of the X-ray CT apparatus 100 to input various types of instructions and various types of settings. The input interface 31 is configured to transfer information about the instructions and the settings received from the operator to the processing circuitry 37. For example, the input interface 31 receives, from the operator, an image taking condition for the CT image data, a reconstruction condition used when the CT image data is reconstructed, an image processing condition applied to the CT image data, and the like. Further, the input interface 31 also receives an operation to select a medical examination to be performed on the patient P. In addition, the input interface 31 receives a designating operation to designate a site rendered in an image.

The display 32 is a monitor referenced by the operator and is configured to display the image data generated from the CT image data for the operator and to display a Graphical User Interface (GUI) used for receiving the various types of instructions and the various types of settings from the operator via the input interface 31, under control of the processing circuitry 37. Further, the display 32 is also configured to display a planning screen for a scan plan and a screen of images during a scan.

Under the control of the processing circuitry 37, the scan controlling circuitry 33 is configured to control the projection data acquiring process performed by the gantry 10, by controlling operations of the X-ray radiation controlling circuitry 11, the gantry driving circuitry 16, the data acquiring circuitry 14, and the table driving device 21. More specifically, the scan controlling circuitry 33 is configured to control projection data acquiring processes during an image taking process to acquire a position determining image (a scanogram image) and during a main image taking process (a scan) to acquire an image used for a diagnosis purpose.

The pre-processing circuitry 34 is configured to generate corrected projection data by performing a logarithmic converting process as well as correcting processes such as an offset correcting process, a sensitivity correcting process, a beam hardening correcting process, and the like, on the projection data generated by the data acquiring circuitry 14. More specifically, the pre-processing circuitry 34 generates pieces of corrected projection data both for the projection data of the position determining image and for the projection data acquired by performing the main image taking process that were generated by the data acquiring circuitry 14 and further stores the pieces of corrected projection data into the storage 35.

The storage 35 is configured to store therein the projection data generated by the pre-processing circuitry 34. More specifically, the storage 35 stores therein the projection data of the position determining image and the projection data for the diagnosis purpose acquired by performing the main image taking process that were generated by the pre-processing circuitry 34. Further, the storage 35 is configured to store therein CT image data reconstructed by the image reconstructing circuitry 36 (explained later), and the like. Further, the storage 35 is configured to store therein a processing result obtained by the processing circuitry 37 (explained later), as appropriate.

The image reconstructing circuitry 36 is configured to reconstruct the CT image data by using the projection data stored in the storage 35. More specifically, the image reconstructing circuitry 36 reconstructs pieces of CT image data both from the projection data of the position determining image and from the projection data of the image for the diagnosis purpose. In this situation, any of various methods can be used as the reconstructing method. For example, a back projection process may be used. Further, examples of the back projection process include a back projection process using a Filtered Back Projection (FBP) method. Alternatively, the image reconstructing circuitry 36 may reconstruct the CT image data by using a successive approximation method.

Further, the image reconstructing circuitry 36 is configured to generate image data by performing various types of image processing processes on the CT image data. After that, the image reconstructing circuitry 36 stores the reconstructed CT image data and the image data generated by performing the various types of image processing processes, into the storage 35.

The processing circuitry 37 is configured to exercise overall control of the X-ray CT apparatus 100 by controlling operations of the gantry 10, the table device 20, and the console 30. More specifically, the processing circuitry 37 is configured to control a CT scan performed by the gantry 10, by controlling the scan controlling circuitry 33. Also, the processing circuitry 37 is configured to control the image reconstruction process and the image generating process performed by the console 30, by controlling the image reconstructing circuitry 36. Further, the processing circuitry 37 is configured to exercise control so that the display 32 displays any of the various types of image data stored in the storage 35.

Further, as illustrated in FIG. 19, the processing circuitry 37 is configured to execute a controlling function 37a, a calculating function 37b, and a display controlling function 37c. The controlling function 37a is configured to control the entirety of the X-ray CT apparatus 100 and also to perform the same processes as those performed by the controlling function 351 described above. The calculating function 37b is configured to perform the same processes as those performed by the calculating function 352 described above. The display controlling function 37c is configured to perform the same processes as those performed by the display controlling function 353 described above.

In the embodiments above, the example is explained in which the single processing circuitry (the processing circuitry 350 or the processing circuitry 37) realizes the processing functions; however, possible embodiments are not limited to this example. For instance, the processing circuitry 350 and the processing circuitry 37 may each be structured by combining a plurality of independent processors, so that each of the processors realizes the processing functions thereof by executing a corresponding one of the programs. Further, the processing functions of the processing circuitry 350 and the processing circuitry 37 may be realized as being distributed or integrated, as appropriate, into a single processing circuit or a plurality of processing circuits. For example, the calculating function 352 may be realized as being distributed into a calculating function and a representative value extracting function.

Further, the term "processor" used in the explanation of the above embodiments denotes, for example, a circuit such as a Central Processing Unit (CPU), a Graphics Processing Unit (GPU), an Application Specific Integrated Circuit (ASIC), or a programmable logic device (e.g., a Simple Programmable Logic Device [SPLD], a Complex Programmable Logic Device [CPLD], or a Field Programmable Gate Array [FPGA]). In this situation, instead of storing the programs in the storage, it is also acceptable to have the programs directly incorporated in the circuits of the processors. In that situation, each of the processors realizes the function thereof by reading the program incorporated in the circuit thereof and executing the read program. The processors according to the present embodiments each do not necessarily have to individually be configured as a single circuit. It is also acceptable to structure a single processor by combining together a plurality of independent circuits so as to realize the functions thereof.

In this situation, the programs executed by the processors are provided as being incorporated, in advance, in a Read-Only Memory, a storage, or the like. The programs may be provided as being recorded on a computer-readable storage medium such as a Compact Disk Read-Only Memory (CD-ROM), a Flexible Disk (FD), a Compact Disk Recordable (CD-R), a Digital Versatile Disk (DVD), or the like, in a file in an installable or executable format for the device. Further, the programs may be provided or distributed as being stored in a computer connected to a network such as the Internet and being downloaded via the network. For example, the programs are structured as a module including functional units. In the actual hardware, as a result of a CPU reading and executing the programs from the storage medium such as a ROM, the modules are loaded into a main storage device and are created in the main storage device.

According to at least one aspect of the embodiments explained above, it is possible to improve the efficiency of the diagnosing processes related to the blood flow.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus comprising:
   processing circuitry configured to:
   obtain image data rendering a blood vessel of a patient,
   receive an instruction from a user interface that represents virtually changing a shape of the blood vessel,
   perform a fluid analysis on the image data in which the shape of the blood vessel is virtually changed and calculate an index value related to a blood flow in the blood vessel after the virtual change with respect to each of a plurality of positions in the blood vessel after the virtual change,
   determine, as a representative position on the blood vessel after the virtual change, a position located at a proximate region on a distal side of a position where the shape has been changed by the virtual change,
   select a representative value at the representative position from among the index values in positions, and
   cause a display to display the representative value in a predetermined display region thereof used for displaying the representative value.

2. The medical information processing apparatus according to claim 1, wherein the index value is a fractional flow reserve value calculated with respected to the blood vessel by performing the fluid analysis.

3. The medical information processing apparatus according to claim 1, wherein the processing circuitry is further configured to
   perform a fluid analysis on the image data and calculate an index value related to a blood flow in the blood vessel before the virtual change with respect to each of a plurality of positions in the blood vessel before the virtual change, analyze a shape of the blood vessel of the patient and set a position in the blood vessel from which an index value is to be displayed on the basis of the shape of the blood vessel, and cause the display to display the index value of the set position.

4. The medical information processing apparatus according to claim 1, wherein the processing circuitry is further configured to perform a fluid analysis on the image data and calculate an index value related to a blood flow in the blood vessel before the virtual change with respect to each of a plurality of positions in the blood vessel before the virtual change, analyze a shape of the blood vessel of the patient and set a position away from a distal position of the blood vessel by a predetermined distance, as the position in the blood vessel from which an index value is to be displayed, and cause the display to display the index value of the set position.

5. The medical information processing apparatus according to claim 1, wherein the processing circuitry is further configured to perform a fluid analysis on the image data and calculate an index value related to a blood flow in the blood vessel before the virtual change with respect to each of a plurality of positions in the blood vessel before the virtual change, analyze a shape of the blood vessel of the patient and set such a position that has a blood vessel diameter equal to a predetermined value and is closest to a distal end, as the position in the blood vessel from which an index value is to be displayed, and cause the display to display the index value of the set position.

6. The medical information processing apparatus according to claim 1, wherein the processing circuitry is further configured to perform a fluid analysis on the image data and calculate an index value related to a blood flow in the blood vessel before the virtual change with respect to each of a plurality of positions in the blood vessel before the virtual change, determine a smallest value among the index values related to the blood flow in the blood vessel as an index value to be displayed, and cause the display to display the smallest value.

7. The medical information processing apparatus according to claim 1, wherein the processing circuitry is further configured to perform a fluid analysis on the image data and calculate an index value related to a blood flow in the blood vessel before the virtual change with respect to each of a plurality of positions in the blood vessel before the virtual change, set such a position where, with respect to the index values exhibited in positions in the blood vessel, a change amount in the index value along an extending direction of the blood vessel exceeds a threshold value, as the position in the blood vessel from which an index value is to be displayed, and cause the display to display the index value of the set position.

8. The medical information processing apparatus according to claim 1, wherein the processing circuitry is further configured to perform a fluid analysis on the image data and calculate an index value related to a blood flow in the blood vessel before the virtual change with respect to each of a plurality of positions in the blood vessel before the virtual change, analyze a shape of the blood vessel and set such a position where a change amount in a cross-sectional area of the blood vessel along an extending direction of the blood vessel exceeds a threshold value, as the position in the blood vessel from which an index value is to be displayed, and cause the display to display the index value of the set position.

9. The medical information processing apparatus according to claim 1, wherein the processing circuitry is further configured to perform a fluid analysis on the image data and calculate an index value related to a blood flow in the blood vessel before the virtual change with respect to each of a plurality of positions in the blood vessel before the virtual change, analyze the blood vessel of the patient and set a position on a distal-end side of a lesion site included in the blood vessel, as the position in the blood vessel from which an index value is to be displayed, and cause the display to display the index value of the set position.

10. The medical information processing apparatus according to claim 1, wherein the processing circuitry is further configured to perform a fluid analysis on the image data and calculate an index value related to a blood flow in the blood vessel before the virtual change with respect to each of a plurality of positions in the blood vessel before the virtual change, set a position of interest in the blood vessel, as the position in the blood vessel from which an index value is to be displayed, and cause the display to display the index value of the set position.

11. The medical information processing apparatus according to claim 10, wherein the position of interest is a position based on one selected from among the following: a position in the blood vessel included in past information of the patient; a position in which a treatment was applied to the blood vessel; and a position designated prior to a treatment applied to the blood vessel.

12. The medical information processing apparatus according to claim 1, wherein the processing circuitry is further configured to extract an index value to be displayed with respect to each of two or more of the blood vessels.

13. The medical information processing apparatus according to claim 1, wherein the processing circuitry is further configured to extract an index value to be displayed with respect to either each of predetermined regions or each of sections defined by a predetermined distance in the blood vessel.

14. The medical information processing apparatus according to claim 1, wherein the processing circuitry is further configured to indicate the representative value in a schematic diagram illustrating an anatomical characteristic of the blood vessel and cause the predetermined display region to display the schematic diagram together with the representative value.

15. The medical information processing apparatus according to claim 1, wherein the processing circuitry is configured to further receive a designating operation to designate a position in the blood vessel rendered in a display image that is generated by using the image data and is displayed in a display region different from the predetermined display region, the processing circuitry is configured to calculate an index value related to the blood flow and exhibited in the position designated by the received designating operation, and cause the predetermined display region to display the index value related to the blood flow and exhibited in the position designated by the designating operation.

16. The medical information processing apparatus according to claim 15, wherein the processing circuitry is configured to change a display mode of a value between when displaying the index value related to the blood flow and exhibited in the position designated by the designating operation and when displaying the representative value.

17. The medical information processing apparatus according to claim 1, wherein the processing circuitry is configured to further receive a predetermined input operation performed in a display region of the display, and the processing circuitry is configured to switch display information in the display region of the display to the representative value, in response to the receiving of the predetermined input operation.

18. The medical information processing apparatus according to claim 1, wherein the processing circuitry is configured to further receive a predetermined input operation performed in a display region of the display, and the processing circuitry is configured to switch display information in the display region of the display into a chart indicating the index value related to the blood flow in the blood vessel, in response to the receiving of the predetermined input operation.

19. The medical information processing apparatus according to claim 17, wherein the processing circuitry is configured to further receive a saving operation to save the display information displayed by the display, and when having received the saving operation, the processing circuitry is configured to output pieces of display information displayed by the display before and after the switching, each as a piece of image information.

20. The medical information processing apparatus according to claim 1, wherein the processing circuitry is configured to further calculate at least one selected from between: an index value difference obtained by calculating a difference in the index value between two or more positions in the blood vessel; and a stenosis percentage value with respect to each of different positions in the blood vessel, and the processing circuitry is configured to cause a display region of the display to further display at least one selected from between the index value difference and the stenosis percentage values.

21. The medical information processing apparatus according to claim 1, wherein the processing circuitry is configured to further generate a display image by using the image data, the processing circuitry is configured to generate the display image in accordance with a result of the calculation, and cause a display region of the display to display the generated display image.

22. The medical information processing apparatus according to claim 21, wherein the processing circuitry is configured to generate at least one selected from between: a display image indicating, in a straight-on position, either a position exhibiting a smallest value as the index value related to the blood flow in the blood vessel or a position exhibiting a largest value as an index value difference obtained by calculating a difference in the index value between two or more positions in the blood vessel; and a display image indicating a cross-section taken at either the position exhibiting the smallest value as the index value or the position exhibiting the largest value as the index value difference.

23. The medical information processing apparatus according to claim 10, wherein the processing circuitry is configured to further generate a display image by using the image data, the processing circuitry is configured to generate the display image indicating, in a straight-on position, a position of interest within the blood vessel, and cause a display region of the display to display the generated display image.

24. The medical information processing apparatus according to claim 1, wherein the processing circuitry is configured to further generate a display image by using the image data, and the processing circuitry is configured to select the position in which the index value is to be displayed, in accordance with an orientation of the blood vessel indicated in the display image.

25. The medical information processing apparatus according to claim 1, wherein the processing circuitry is configured to arrange the index value at a predetermined site of the blood vessel to be in a non-display state.

26. The medical information processing apparatus according to claim 25, wherein the predetermined site of the blood vessel includes a plaque region, a bypass region, a bridge region, a calcified region, or an image artifact region of the blood vessel.

27. The medical information processing apparatus according to claim 1, wherein the processing circuitry is further configured to perform a fluid analysis on the image data and calculate an index value related to a blood flow in the blood vessel before the virtual change with respect to each of a plurality of positions in the blood vessel before the virtual change, calculate a distal-end position in which a pressure wire is able to measure pressure in the blood vessel, on the basis of structure information of the blood vessel and structure information of the pressure wire, select the index value at the distal-end position in which the pressure wire is able to measure the pressure, as an index value to be displayed, and cause the display to display the index value of the set position.

28. The medical information processing apparatus according to claim 27, wherein the processing circuitry is configured to calculate the distal-end position in which the pressure wire is able to measure the pressure in the blood vessel, on the basis of structure information of the blood vessel and structure information of the pressure wire in a stress state.

29. The medical information processing apparatus according to claim 27, wherein the processing circuitry is configured to further receive a designating operation to designate a position in the blood vessel rendered in a display image generated by using the image data, and the processing circuitry is configured to change display modes of a GUI used for receiving the designating operation and the index value, depending on whether or not the position designated by the designating operation is a position in which the pressure wire is able to measure the pressure.

30. An X-ray CT apparatus comprising:

processing circuitry configured to:

acquire image data rendering a blood vessel of a patient, receive an instruction from a user interface that represents virtually changing a shape of the blood vessel, perform a fluid analysis on the image data in which the shape of the blood vessel is virtually changed and calculate an index value related to a blood flow in the blood vessel after the virtual change with respect to each of a plurality of positions in the blood vessel after the virtual change, determine, as a representative position on the blood vessel after the virtual change, a position located at a proximate region on a distal side of a position where the shape has been changed by the virtual change, select a representative value at the representative position from among the index values in positions, and cause a display to display the representative value in a predetermined display region thereof used for displaying the representative value.

31. A medical information processing method comprising:

obtaining image data rendering a blood vessel of a patient;

receiving an instruction from a user interface that represents virtually changing a shape of the blood vessel;

performing a fluid analysis on the image data in which the shape of the blood vessel is virtually changed and calculating an index value related to a blood flow in the blood vessel after the virtual change with respect to each of a plurality of positions in the blood vessel after the virtual change; determining, as a representative position on the blood vessel after the virtual change, a position located at a proximate region on a distal side of a position where the shape has been changed by the virtual change;

selecting a representative value at the representative position from among the index values in positions; and causing a display to display the representative value in a predetermined display region thereof used for displaying the representative value.

* * * * *